US012702840B2

(12) United States Patent
Single et al.

(10) Patent No.: US 12,702,840 B2
(45) Date of Patent: Aug. 11, 2026

(54) PROGRAMMING OF NEUROMODULATION THERAPY

(71) Applicant: Saluda Medical Pty Ltd, Macquarie Park (AU)

(72) Inventors: Peter Scott Vallack Single, Artarmon (AU); Robert Bruce Gorman, Artarmon (AU); Daniel John Parker, Artarmon (AU); Samuel Nicholas Gilbert, Artarmon (AU); Thomas Michael Damjanovic, Artarmon (AU)

(73) Assignee: Saluda Medical Pty Ltd, Macquarie Park (AU)

(*) Notice: Subject to any disclaimer, the term of this patent is extended or adjusted under 35 U.S.C. 154(b) by 219 days.

(21) Appl. No.: 18/689,953

(22) PCT Filed: Sep. 12, 2022

(86) PCT No.: PCT/AU2022/051100
§ 371 (c)(1),
(2) Date: Mar. 7, 2024

(87) PCT Pub. No.: WO2023/035043
PCT Pub. Date: Mar. 16, 2023

(65) Prior Publication Data

US 2024/0382758 A1 Nov. 21, 2024

(30) Foreign Application Priority Data

Sep. 10, 2021 (AU) ................................ 2021902938

(51) Int. Cl.
*A61N 1/36* (2006.01)

(52) U.S. Cl.
CPC ....... *A61N 1/36139* (2013.01); *A61N 1/3615* (2013.01)

(58) Field of Classification Search
CPC ............ A61N 1/36071; A61N 1/36062; A61N 1/36139; A61N 1/3615
See application file for complete search history.

(56) References Cited

U.S. PATENT DOCUMENTS 6,909,917 B2 6/2005 Woods et al.
7,343,200 B2 3/2008 Litvak et al.
(Continued)

FOREIGN PATENT DOCUMENTS

CN 110870945 A 3/2020
EP 3171929 B1 5/2017
(Continued)

OTHER PUBLICATIONS

Danner et al., Body Position Influences Which Neural Structures Are Recruited by Lumbar Transcutaneous Spinal Cord Stimulation, PLOS ONE, 11(1), 2016, pp. 1-13.
(Continued)

*Primary Examiner* — George R Evanisko
(74) *Attorney, Agent, or Firm* — Barnes & Thornburg LLP

(57) ABSTRACT

A neuromodulation system and method. An implantable electrode array comprises a plurality of electrodes. A stimulus source provides neural stimuli delivered via stimulus electrodes to neural tissue to evoke neural responses. Measurement circuitry captures signal windows sensed from the neural tissue subsequent to each stimulus. A control unit controls the neural stimuli according to a stimulus intensity parameter. A processor introduces a perturbation to the parameter from a baseline stimulus intensity. A time series of intensities of the evoked neural responses is obtained, from which a time series of estimates of at least one physiological characteristic of the neural tissue is obtained. Each physiological characteristic being variable as a result of a posture wave. A baseline value of each physiological
(Continued)

characteristic is estimated from the time series of estimates of each physiological characteristic.

19 Claims, 19 Drawing Sheets

(56) References Cited

U.S. PATENT DOCUMENTS

| | | | | |
|---|---|---|---|---|
| 7,616,999 | B2 | 11/2009 | Overstreet et al. | |
| 7,801,615 | B2 | 9/2010 | Meadows et al. | |
| 8,843,209 | B2 | 9/2014 | Wacnik et al. | |
| 9,155,892 | B2 | 10/2015 | Parker et al. | |
| 9,314,202 | B2 | 4/2016 | Choi | |
| 9,375,574 | B2 | 6/2016 | Kaula et al. | |
| 9,387,325 | B1 | 7/2016 | Min et al. | |
| 9,907,957 | B2 | 3/2018 | Woods et al. | |
| 10,279,182 | B2 | 5/2019 | Hou et al. | |
| 10,500,399 | B2 | 12/2019 | Single | |
| 11,260,232 | B2 | 3/2022 | Kaula et al. | |
| 11,589,810 | B2 | 2/2023 | Gerber et al. | |
| 11,806,538 | B2 | 11/2023 | Kibler et al. | |
| 2008/0221640 | A1 | 9/2008 | Overstreet et al. | |
| 2017/0120056 | A1 | 5/2017 | Woods et al. | |
| 2018/0104493 | A1 | 4/2018 | Doan et al. | |
| 2018/0110987 | A1* | 4/2018 | Parker | A61N 1/36139 |
| 2019/0168000 | A1 | 6/2019 | Laird-Wah | |
| 2021/0379385 | A1 | 12/2021 | Hou et al. | |
| 2022/0212014 | A1 | 7/2022 | Steinke | |
| 2022/0241582 | A1 | 8/2022 | Huertas et al. | |
| 2022/0266033 | A1 | 8/2022 | Jackson et al. | |

FOREIGN PATENT DOCUMENTS

| | | | |
|---|---|---|---|
| WO | WO1992019156 | A1 | 11/1992 |
| WO | WO1997048447 | A1 | 12/1997 |
| WO | WO2001043818 | A1 | 6/2001 |
| WO | WO2006119046 | A1 | 11/2006 |
| WO | WO2009013616 | A2 | 1/2009 |
| WO | WO2009064858 | A1 | 5/2009 |
| WO | WO2014210373 | A1 | 12/2014 |
| WO | WO2015013398 | A1 | 1/2015 |
| WO | WO2015179177 | A1 | 11/2015 |
| WO | WO2016048967 | A1 | 3/2016 |
| WO | WO2017048963 | A1 | 3/2017 |
| WO | WO2018053336 | A1 | 3/2018 |
| WO | WO2019136072 | A1 | 7/2019 |
| WO | WO2019190710 | A1 | 10/2019 |
| WO | WO2020010120 | A1 | 1/2020 |
| WO | WO2020087123 | A1 | 5/2020 |
| WO | WO2021021325 | A1 | 2/2021 |
| WO | WO2021021326 | A1 | 2/2021 |
| WO | WO2021021327 | A1 | 2/2021 |
| WO | WO2021126431 | A1 | 6/2021 |
| WO | WO2021126432 | A1 | 6/2021 |
| WO | WO2021126433 | A1 | 6/2021 |
| WO | WO2021126587 | A1 | 6/2021 |
| WO | WO2021126588 | A1 | 6/2021 |
| WO | WO2021146778 | A1 | 7/2021 |
| WO | WO2022150638 | A1 | 7/2022 |
| WO | WO2022204650 | A1 | 9/2022 |

OTHER PUBLICATIONS

International Search Report and Written Opinion in PCT/AU2022/051100, dated Dec. 23, 2022, 23 pages.
Kim, M.W. et al., The Effect of Wrist Position on the Conduction Velocity of the Ulnar Nerve, Journal of the Korean Academy of Rehabilitation Medicine, 2003, 27(5), pp. 708-711.
Mahnam et al., Measurement of the current-distance relationship using a novel refractory interaction technique, J. Neural Eng. 6(2): 036005, published May 20, 2009, 22 pgs.
Nehme et al., Measures of the electrically evoked compound action potential threshold and slope in HiRes, Cochlear Implants International vol. 15 No. 1 (2014) pp. 53-60.
Olin et al., Postural Changes in Spinal Cord Stimulation Perceptual Thresholds, Neuromodulation, vol. 1 , No. 4, 1998, pp. 171-175.
Pilitsis et al., The Evoked Compound Action Potential as a Predictor for Perception in Chronic Pain Patients: Tools for Automatic Spinal Cord Stimulator Programming and Control, Frontiers in Neuroscience, vol. 15, Jul. 2021, pp. 1-11.
Examination Report in EP 22865957.9, dated Feb. 19, 2026, 11 pages.

* cited by examiner

Fig. 18

PROGRAMMING OF NEUROMODULATION THERAPY

CROSS-REFERENCE TO RELATED APPLICATIONS

This is a 371 national stage of International Patent Application No. PCT/AU2022/051100, filed Sep. 12, 2022, which claims the benefit of Australian Provisional Patent Application No. 2021902938, filed Sep. 10, 2021, which applications are incorporated herein by reference in their entirety.

TECHNICAL FIELD

The present invention relates to neuromodulation therapy and in particular to selecting appropriate neuromodulation therapy settings for a particular patient.

BACKGROUND OF THE INVENTION

There are a range of situations in which it is desirable to apply neural stimuli in order to alter neural function, a process known as neuromodulation. For example, neuromodulation is used to treat a variety of disorders including chronic neuropathic pain, Parkinson's disease, and migraine. A neuromodulation system applies an electrical pulse (stimulus) to neural tissue (fibres, or neurons) in order to generate a therapeutic effect. In general, the electrical stimulus generated by a neuromodulation system evokes a neural response known as an action potential in a neural fibre which then has either an inhibitory or excitatory effect. Inhibitory effects can be used to modulate an undesired process such as the transmission of pain, or excitatory effects may be used to cause a desired effect such as the contraction of a muscle.

When used to relieve neuropathic pain originating in the trunk and limbs, the electrical pulse is applied to the dorsal column (DC) of the spinal cord, a procedure referred to as spinal cord stimulation (SCS). Such a system typically comprises an implanted electrical pulse generator, and a power source such as a battery that may be transcutaneously rechargeable by wireless means, such as inductive transfer. An electrode array is connected to the pulse generator, and is implanted adjacent the target neural fibre(s) in the spinal cord, typically in the dorsal epidural space above the dorsal column. An electrical pulse of sufficient intensity applied to the target neural fibres by a stimulus electrode causes the depolarisation of neurons in the fibres, which in turn generates an action potential in the fibres. Action potentials propagate along the fibres in orthodromic (in afferent fibres this means towards the head, or rostral) and antidromic (in afferent fibres this means towards the cauda, or caudal) directions. The fibres being stimulated in this way inhibit the transmission of pain from a region of the body innervated by the target neural fibres (the dermatome) to the brain. To sustain the pain relief effects, stimuli are applied repeatedly, for example at a frequency in the range of 30 Hz-100 Hz.

For effective and comfortable neuromodulation, it is necessary to maintain stimulus intensity above a recruitment threshold. Stimuli below the recruitment threshold will fail to recruit sufficient neurons to generate action potentials with a therapeutic effect. In almost all neuromodulation applications, response from a single class of fibre is desired, but the stimulus waveforms employed can evoke action potentials in other classes of fibres which cause unwanted side effects. In pain relief, it is therefore desirable to apply stimuli with intensity below a discomfort threshold, above which uncomfortable or painful percepts arise due to over-recruitment of Aβ fibres. When recruitment is too large, Aβ fibres produce uncomfortable sensations. Stimulation at high intensity may even recruit Aδ fibres, which are sensory nerve fibres associated with acute pain, cold and pressure sensation. It is therefore desirable to maintain stimulus intensity within a therapeutic range between the recruitment threshold and the discomfort threshold.

The task of maintaining appropriate neural recruitment is made more difficult by electrode migration (change in position over time) and/or postural changes of the implant recipient (patient), either of which can significantly alter the neural recruitment arising from a given stimulus, and therefore the therapeutic range. There is room in the epidural space for the electrode array to move, and such array movement from migration or posture change alters the electrode-to-fibre distance and thus the recruitment efficacy of a given stimulus. Moreover, the spinal cord itself can move within the cerebrospinal fluid (CSF) with respect to the dura. During postural changes, the amount of CSF and/or the distance between the spinal cord and the electrode can change significantly. This effect is so large that postural changes alone can cause a previously comfortable and effective stimulus regime to become either ineffectual or painful.

Another control problem facing neuromodulation systems of all types is achieving neural recruitment at a sufficient level for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the implanted lifetime of the device.

Attempts have been made to address such problems by way of feedback or closed-loop control, such as using the methods set forth in International Patent Publication No. WO 2012/155188 by the present applicant, the content of which is incorporated herein by reference. Feedback control seeks to compensate for relative nerve/electrode movement by controlling the intensity of the delivered stimuli so as to maintain a substantially constant neural recruitment. The intensity of a neural response evoked by a stimulus may be used as a feedback variable representative of the amount of neural recruitment. A signal representative of the neural response may be sensed by a measurement electrode in electrical communication with the recruited neural fibres, and processed to obtain the feedback variable. Based on the response intensity, the intensity of the applied stimulus may be adjusted to maintain the response intensity within a therapeutic range.

It is therefore desirable to accurately detect and record a neural response evoked by the stimulus. The action potentials generated by the depolarisation of a large number of fibres by a stimulus sum to form a measurable signal known as an evoked compound action potential (ECAP). Accordingly, an ECAP is the sum of responses from a large number of single fibre action potentials. The ECAP generated from the depolarisation of a group of similar fibres may be measured at a measurement electrode as a positive peak potential, then a negative peak, followed by a second positive peak. This morphology is caused by the region of activation passing the measurement electrode as the action potentials propagate along the individual fibres.

Approaches proposed for obtaining a neural response measurement are described by the present applicant in International Patent Publication No. WO 2012/155183, the content of which is incorporated herein by reference.

Patient characteristics that are important for closed-loop SCS therapy vary significantly between patients. It is therefore beneficial to tailor or personalise SCS therapy to each individual patient. This is typically done soon after implantation, before the patient returns home, in a procedure known as programming, or fitting. Programming involves a trained clinician interacting with the patient, utilising wireless access to the implanted pulse generator to apply various neural stimuli, and inquiring about the effects. Over many iterations, the best therapy parameters for the condition of the patient may be arrived at. These parameters may then be downloaded to the pulse generator and thereafter used to govern the therapy administered to the patient out of the clinic. As programming can be a laborious and time-consuming process, it is beneficial to carry it out as swiftly and painlessly as possible. In addition to this overriding need, the programming needs to be able to handle not only the variations between patients, but the variations over time that a particular patient is likely to experience once out of clinic and taking part in daily activities.

Therefore, a need exists for a programming procedure that is time-efficient, comfortable for the patient, and flexible enough to accommodate variations in the physiological characteristics of the patient that are important for SCS.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word “comprise”, or variations such as “comprises” or “comprising”, will be understood to imply the inclusion of a stated element, integer or step, or group of elements, integers or steps, but not the exclusion of any other element, integer or step, or group of elements, integers or steps.

In this specification, a statement that an element may be “at least one of” a list of options is to be understood to mean that the element may be any one of the listed options, or may be any combination of two or more of the listed options.

SUMMARY OF THE INVENTION

Disclosed herein are systems for, and methods of, programming an SCS device by estimating physiological characteristics of the patient that relate to closed-loop SCS therapy in a manner that is time-efficient and not uncomfortable for the patient. Of particular concern for the present technology are patients in whom the natural variation of such characteristics over the heartbeat and breathing cycles is larger than normal due to the location of their implanted electrodes. The disclosed methods make use of open-loop or closed-loop neural stimulation, or both, to estimate baseline values for, and optionally ranges of variation of, the physiological characteristics by observing the variations in the neural response that result either from application of a controlled stimulus or the natural variation of the physiological characteristics due to the heartbeat and/or breathing cycles.

According to a first aspect of the present technology, there is provided a neuromodulation system comprising: an implantable electrode array comprising a plurality of electrodes; a stimulus source configured to provide neural stimuli to be delivered via one or more stimulus electrodes to neural tissue proximal to the implantable electrode array in order to evoke neural responses from the neural tissue, the one or more stimulus electrodes being selected from the plurality of electrodes; measurement circuitry configured to capture signal windows sensed from the neural tissue via one or more sense electrodes subsequent to respective neural stimuli, the one or more sense electrodes being selected from the plurality of electrodes; a control unit configured to control the stimulus source to provide the neural stimuli according to respective values of a stimulus intensity parameter; and a processor configured to: instruct the control unit to control the stimulus source to provide the neural stimuli according to values of the stimulus intensity parameter that comprise a perturbation from a baseline stimulus intensity; process the captured signal windows from the measurement circuitry in order to measure a time series of intensities of the evoked neural responses; extract, using the measured neural response intensity time series, time series of estimates of at least one physiological characteristic of the neural tissue, wherein each physiological characteristic varies around a baseline value as a result of a posture wave; and estimate the baseline value of each physiological characteristic from the time series of estimates of each physiological characteristic.

According to a second aspect of the present technology, there is provided a method of estimating a baseline value of one or more physiological characteristics of a patient, the method comprising: delivering neural stimuli to neural tissue according to respective values of a stimulus intensity parameter in order to evoke neural responses from the neural tissue; perturbing the stimulus intensity parameter by a small amount from a baseline stimulus intensity; capturing signal windows sensed on the neural tissue subsequent to respective neural stimuli; processing the captured signal windows in order to measure a time series of intensities of the evoked neural responses; extracting, using the measured neural response intensity time series, a time series of estimates of at least one physiological characteristic of the neural tissue, wherein each physiological characteristic varies around a baseline value as a result of a posture wave; and estimating the baseline value of each physiological characteristic from the time series of estimates of each physiological characteristic.

According to a third aspect of the present technology, there is provided a neuromodulation system comprising: an implantable electrode array comprising a plurality of electrodes; a stimulus source configured to provide neural stimuli to be delivered via one or more stimulus electrodes to neural tissue proximal to the implantable electrode array in order to evoke neural responses from the neural tissue, the one or more stimulus electrodes being selected from the plurality of electrodes; measurement circuitry configured to capture signal windows sensed from the neural tissue via one or more sense electrodes subsequent to respective neural stimuli, the one or more sense electrodes being selected from the plurality of electrodes; a control unit configured to: control the stimulus source to provide the neural stimuli according to respective values of a stimulus intensity parameter; process each captured signal window from the measurement circuitry in order to measure an intensity of each evoked neural response; and adjust the stimulus intensity parameter so as to bring the measured neural response intensity towards a target neural response intensity; and a processor configured to: extract a representative value of the stimulus intensity parameter corresponding to the target neural response intensity; adjust the target neural response intensity; repeat the extracting and adjusting, yielding a plurality of (representative stimulus intensity, target neural response intensity) pairs; and estimate a baseline value of each of one or more physiological characteristics of the neural tissue from the plurality of (representative stimulus intensity, target neural response intensity) pairs, wherein each physiological characteristic varies around the baseline value as a result of a posture wave.

According to a fourth aspect of the present technology, there is provided a method of estimating a baseline value of one or more physiological characteristics of neural tissue of a patient, the method comprising: delivering neural stimuli to neural tissue of the patient according to respective values of a stimulus intensity parameter in order to evoke neural responses from the neural tissue; setting a target neural response intensity; capturing signal windows sensed on the neural tissue subsequent to respective neural stimuli; processing each captured signal window in order to measure an intensity of each evoked neural response; adjusting the stimulus intensity parameter so as to bring the measured neural response intensity towards the target neural response intensity; extracting a representative value of stimulus intensity parameter corresponding to the target neural response intensity; adjusting the target neural response intensity; repeating the capturing, processing, adjusting, extracting, and adjusting, yielding a plurality of (representative stimulus intensity, target neural response intensity) pairs; and estimating a baseline value of each of one or more physiological characteristics of the neural tissue from the plurality of (representative stimulus intensity, target neural response intensity) pairs, wherein each physiological characteristic varies around the baseline value as a result of a posture wave.

According to a fifth aspect of the present technology, there is provided a neuromodulation system comprising: an implantable electrode array comprising a plurality of electrodes; a stimulus source configured to provide neural stimuli to be delivered via one or more stimulus electrodes to neural tissue proximal to the implantable electrode array in order to evoke neural responses from the neural tissue, the one or more stimulus electrodes being selected from the plurality of electrodes; measurement circuitry configured to capture signal windows sensed from the neural tissue via one or more sense electrodes subsequent to respective neural stimuli, the one or more sense electrodes being selected from the plurality of electrodes; a control unit configured to: control the stimulus source to provide the neural stimuli according to respective values of a stimulus intensity parameter; process each captured signal window from the measurement circuitry in order to measure an intensity of each evoked neural response; and adjust, using a controller gain, the stimulus intensity parameter so as to bring the measured neural response intensity towards a target neural response intensity; and a processor configured to: measure a variation in the measured neural response intensity; and estimate a baseline value of a physiological characteristic of the neural tissue from the measured variation in the neural response intensity, wherein the physiological characteristic varies around a baseline value as a result of a posture wave.

According to a sixth aspect of the present technology, there is provided a method of estimating a baseline value of a physiological characteristic of neural tissue of a patient, the method comprising: delivering neural stimuli to neural tissue of the patient according to respective values of a stimulus intensity parameter in order to evoke neural responses from the neural tissue; setting a target neural response intensity; capturing signal windows sensed on the neural tissue subsequent to respective neural stimuli; processing each captured signal window in order to measure an intensity of each evoked neural response; adjusting the stimulus intensity parameter so as to bring the measured neural response intensity towards the target neural response intensity; measuring a variation in the measured neural response intensity; and estimating a baseline value of the physiological characteristic from the measured variation in the neural response intensity, wherein the physiological characteristic varies around a baseline value as a result of a posture wave.

According to seventh aspect of the present technology, there is provided a non-transitory computer readable medium for estimating a baseline value of one or more physiological characteristics of a patient, the medium comprising instructions which, when executed by one or more processors, causes performance of the method of the second, fourth, or sixth aspect of the present technology.

In some embodiments of the invention, the stimulus intensity parameter perturbation comprises an oscillatory waveform with a period that is short compared to a period of the posture wave. In some embodiments of the invention, the processor is configured to extract the time series of estimates of each physiological characteristic by separating a component of variation of the measured neural response intensity time series that is stimulus-induced from a component of variation of the measured neural response intensity time series that is induced by the posture wave. In some embodiments of the invention, the stimulus intensity parameter perturbation comprises pairs of different intensity separated by an interval that is short compared to a period of the posture wave.

In some embodiments of the invention, the processor is configured to estimate the baseline value of one of the one or more physiological characteristics by forming a histogram of the time series of estimates of the physiological characteristic. In some embodiments of the invention there are a plurality of physiological characteristics, and the processor is configured to estimate the baseline value of each physiological characteristic by forming a joint histogram from the time series of estimates of each physiological characteristic. In some embodiments of the invention, the processor is further configured to estimate a range of variation of one of the one or more physiological characteristics from the time series of estimates of the physiological characteristic. In some embodiments of the invention, the processor is further configured to set a feedback parameter according to the baseline estimate of one of the one or more physiological characteristics.

In some embodiments of the invention, the control unit is further configured to: process each captured signal window from the measurement circuitry in order to measure an intensity of each evoked neural response; and adjust, using the feedback parameter, the stimulus intensity parameter so as to bring the measured neural response intensity towards a target neural response intensity. In such embodiments of the invention, the processor may be further configured to: extract a representative value of stimulus intensity parameter corresponding to the target neural response intensity; adjust the target neural response intensity; and repeat the extracting and adjusting, yielding a plurality of (representative stimulus intensity, target response intensity) pairs. In such embodiments of the invention, the processor may be further configured to: estimate the baseline value of each physiological characteristic from the plurality of (representative stimulus intensity, target response intensity) pairs. In such embodiments of the invention the processor may be further configured to estimate the baseline value of each physiological characteristic by fitting an activation plot to the plurality of (representative stimulus intensity, target response intensity) pairs. In such embodiments of the invention, the one or more physiological characteristics may be a slope and a threshold of the fitted activation plot.

In some embodiments of the invention the processor is further configured to extract a range of variation of the stimulus intensity parameter corresponding to the target neural response intensity. In some embodiments of the invention, the processor is further configured to calculate a confidence interval around the baseline value of each physiological characteristic.

Some embodiments of the invention may further comprise an external computing device configured to communicate with the control unit that is co-located with, and in communication with, the measurement circuitry and the stimulus source within an implantable electronics module. In such embodiments, the processor may be part of the external computing device and may be configured by program instructions stored in an instruction memory of the external computing device. In some embodiments of the invention, the processor is part of the control unit.

In some embodiments of the invention, the processor is configured to perturb the stimulus intensity periodically at a frequency higher than that of the posture wave. In some embodiments of the invention, the processor may be configured to perturb the stimulus intensity at half a frequency of the neural stimuli.

In some embodiments of the invention, measuring a variation in the measured neural response intensity comprises measuring an amplitude of variation of the measured neural response intensity, and the processor is configured to estimate the baseline value of the physiological characteristic by: measuring a gain from an amplitude of the stimulus intensity perturbation to the amplitude of variation in the measured neural response intensity; and estimating the baseline value from the measured gain and the controller gain.

In some embodiments of the invention, the processor is configured to perturb the stimulus intensity by a step. In some embodiments of the invention, measuring a variation in the measured neural response intensity comprises measuring a transient response of the measured neural response intensity to the perturbation of the stimulus intensity, and wherein the processor is configured to estimate the baseline value from the transient response of the measured neural response intensity and the controller gain.

In some embodiments of the invention, measuring a variation in the measured neural response intensity comprises measuring a variation in the measured neural response intensity at a first value of the controller gain, and the processor is further configured to measure a variation in the measured neural response intensity at a second value of the controller gain. In such embodiments of the invention, the processor may be configured to estimate the baseline value of the physiological characteristic by: computing an amount of attenuation in the variation in the measured neural response intensity between the first and second values of the controller gain; and estimating the baseline value from the amount of attenuation and the first and second values of the controller gain. In such embodiments of the invention, measuring the variation in the measured neural response intensity may comprise measuring an RMS noise of the measured neural response intensity. In alternative such embodiments of the invention, measuring the variation in the measured neural response intensity may comprise an amplitude of variation of the measured neural response intensity with the posture wave and the processor may optionally be further configured to compute a range of variation of the physiological characteristic from the baseline estimate and the target neural response intensity.

In some embodiments of the invention, a first value of the controller gain is zero. In some embodiments of the invention, the processor may be further configured to adjust the controller gain based on the baseline estimate of the physiological characteristic.

The following are examples of the invention:

Example 1. A neuromodulation system comprising: an implantable electrode array comprising a plurality of electrodes; a stimulus source configured to provide neural stimuli to be delivered via one or more stimulus electrodes to neural tissue proximal to the implantable electrode array, the one or more stimulus electrodes being selected from the plurality of electrodes; measurement circuitry configured to capture signal windows sensed from the neural tissue via one or more sense electrodes subsequent to respective neural stimuli, the one or more sense electrodes being selected from the plurality of electrodes; a control unit configured to control the stimulus source to provide the neural stimuli according to respective values of a stimulus intensity parameter; and a processor configured to: instruct the control unit to control the stimulus source to provide the neural stimuli according to values of the stimulus intensity parameter that vary rapidly by a small amount from a baseline stimulus intensity; process the captured signal windows from the measurement circuitry in order to measure a time series of intensities of the evoked neural responses; extract, using the measured neural response intensity time series, time series of estimates of at least one physiological characteristic of the neural tissue, wherein each physiological characteristic varies around a baseline value as a result of a posture wave; and estimate the baseline value of each physiological characteristic from the time series of estimates of each physiological characteristic.

Example 2. The neuromodulation system of example 1, wherein the stimulus intensity parameter varies rapidly according to an oscillatory waveform with a period that is short compared to a period of the posture wave.

Example 3. The neuromodulation system of example 2, wherein the processor is configured to extract the time series of estimates of each physiological characteristic by separating a component of variation of the measured neural response intensity time series that is stimulus-induced from a component of variation of the measured neural response intensity time series that is induced by the posture wave.

Example 4. The neuromodulation system of example 1, wherein the stimulus intensity parameter varies rapidly in pairs of different intensity separated by an interval that is short compared to a period of the posture wave.

Example 5. The neuromodulation system of any one of examples 1 to 4, wherein the processor is configured to estimate the baseline value of one of the one or more physiological characteristics by forming a histogram of the time series of estimates of the physiological characteristic.

Example 6. The neuromodulation system of any one of examples 1 to 4, wherein there are a plurality of physiological characteristics, and the processor is configured to estimate the baseline value of each physiological characteristic by forming a joint histogram from the time series of estimates of each physiological characteristic.

Example 7. The neuromodulation system of any one of examples 1 to 6, wherein the processor is further configured to estimate a range of variation of one of the one or more physiological characteristics from the time series of estimates of the physiological characteristic.

Example 8. The neuromodulation system of any one of examples 1 to 7, wherein the processor is further configured to set a feedback parameter according to the baseline estimate of one of the one or more physiological characteristics.

Example 9. The neuromodulation system of example 8, wherein the control unit is further configured to: process each captured signal window from the measurement circuitry in order to measure an intensity of each evoked neural response; adjust, using the feedback parameter, the stimulus intensity parameter so as to bring the measured neural response intensity towards a target neural response intensity.

Example 10. The neuromodulation system of example 9, wherein the processor is further configured to: extract a representative value of stimulus intensity parameter corresponding to the target neural response intensity; and adjust the target neural response intensity; repeat the extracting and adjusting, yielding a plurality of (representative stimulus intensity, target response intensity) pairs.

Example 11. The neuromodulation system of example 10, wherein the processor is further configured to estimate the baseline value of each physiological characteristic from the plurality of (representative stimulus intensity, target response intensity) pairs.

Example 12. The neuromodulation system of example 11, wherein the processor is configured to estimate the baseline value of each physiological characteristic by fitting an activation plot to the plurality of (representative stimulus intensity, target response intensity) pairs.

Example 13. The neuromodulation system of example 12, wherein the one or more physiological characteristics are a slope and a threshold of the fitted activation plot.

Example 14. The neuromodulation system of any one of examples 12 to 13, wherein the processor is further configured to calculate a confidence interval around the baseline value of each physiological characteristic.

Example 15. The neuromodulation system of any one of examples 1 to 14, further comprising an external computing device configured to communicate with the control unit that is co-located with, and in communication with, the measurement circuitry and the stimulus source within an implantable electronics module.

Example 16. The neuromodulation system of example 15, wherein the processor is part of the external computing device and is configured by program instructions stored in an instruction memory of the external computing device.

Example 17. A method of estimating a baseline value of one or more physiological characteristics of a patient, the method comprising: delivering neural stimuli to neural tissue according to respective values of a stimulus intensity parameter in order to evoke neural response from the neural tissue; rapidly varying the stimulus intensity parameter by a small amount from a baseline stimulus intensity; capturing signal windows sensed on the neural tissue subsequent to respective neural stimuli; processing the captured signal windows in order to measure a time series of intensities of the evoked neural responses; extracting, using the measured neural response intensity time series, a time series of estimates of at least one physiological characteristic of the neural tissue, wherein each physiological characteristic varies around a baseline value as a result of a posture wave; and estimating the baseline value of each physiological characteristic from the time series of estimates of each physiological characteristic.

Example 18. A non-transitory computer readable medium for estimating a baseline value of one or more physiological characteristics of a patient, the medium comprising instructions which, when executed by one or more processors, causes performance of the following: delivering neural stimuli to neural tissue according to respective values of a stimulus intensity parameter in order to evoke neural response from the neural tissue; rapidly varying the stimulus intensity parameter by a small amount from a baseline stimulus intensity; capturing signal windows sensed on the neural tissue subsequent to respective neural stimuli; process the captured signal windows in order to measure a time series of intensities of the evoked neural responses; extract, using the measured neural response intensity time series, time series of estimates of at least one physiological characteristic of the neural tissue, wherein each physiological characteristic varies around a baseline value as a result of a posture wave; and estimate the baseline value of each physiological characteristic from the time series of estimates of each physiological characteristic.

Example 16. A neuromodulation system comprising: an implantable electrode array comprising a plurality of electrodes; a stimulus source configured to provide neural stimuli to be delivered via one or more stimulus electrodes to neural tissue proximal to the implantable electrode array, the one or more stimulus electrodes being selected from the plurality of electrodes; measurement circuitry configured to capture signal windows sensed from the neural tissue via one or more sense electrodes subsequent to respective neural stimuli, the one or more sense electrodes being selected from the plurality of electrodes; a control unit configured to: control the stimulus source to provide the neural stimuli according to respective values of a stimulus intensity parameter; process each captured signal window from the measurement circuitry in order to measure an intensity of each evoked neural response; and adjust the stimulus intensity parameter so as to bring the measured neural response intensity towards the target neural response intensity; and a processor configured to: extract a representative value of stimulus intensity parameter corresponding to the target neural response intensity; adjust the target neural response intensity; repeat the extracting and adjusting, yielding a plurality of (representative stimulus intensity, target response intensity) pairs; and estimate a baseline value of each of one or more physiological characteristics from the plurality of (representative stimulus intensity, target response intensity) pairs, wherein each physiological characteristic varies around the baseline value as a result of a posture wave.

Example 17. The neuromodulation system of example 16, wherein the processor is configured to estimate the baseline value of each physiological characteristic by fitting an activation plot to the plurality of (representative stimulus intensity, target response intensity) pairs.

Example 18. The neuromodulation system of example 17, wherein the one or more physiological characteristics are a slope and a threshold of the fitted activation plot.

Example 19. The neuromodulation system of any one of examples 17 to 18, wherein the processor is further configured to calculate a confidence interval around the baseline value of each physiological characteristic.

Example 20. The neuromodulation system of any one of examples 16 to 19, further comprising an external computing device configured to communicate with the control unit is co-located with, and in communication with, the measurement circuitry and the stimulus source within an implantable electronics module.

Example 21. The neuromodulation system of example 20, wherein the processor is part of the external computing device and is configured by program instructions stored in an instruction memory of the external computing device.

Example 22. A method of estimating a baseline value of one or more physiological characteristics of a patient, the method comprising: delivering neural stimuli to neural tissue according to respective values of a stimulus intensity parameter in order to evoke neural response from the neural tissue; setting a target neural response intensity; capturing signal windows sensed on the neural tissue subsequent to respective neural stimuli; processing each captured signal window in order to measure an intensity of each evoked neural response; adjusting the stimulus intensity parameter so as to bring the measured neural response intensity towards the target neural response intensity; extracting a representative value of stimulus intensity parameter corresponding to the target neural response intensity; adjusting the target neural response intensity; repeating the capturing, processing, adjusting, extracting, and adjusting, yielding a plurality of (representative stimulus intensity, target response intensity) pairs; and estimating a baseline value of each of one or more physiological characteristics of the tissue from the plurality of (representative stimulus intensity, target response intensity) pairs, wherein each physiological characteristic varies around the baseline value as a result of a posture wave.

Example 23. A non-transitory computer readable medium for estimating a baseline value of one or more physiological characteristics of a patient, the medium comprising instructions which, when executed by one or more processors, causes performance of the following: delivering neural stimuli to neural tissue according to respective values of a stimulus intensity parameter in order to evoke neural response from the neural tissue; setting a target neural response intensity; capturing signal windows sensed on the neural tissue subsequent to respective neural stimuli; processing each captured signal window in order to measure an intensity of each evoked neural response; adjusting the stimulus intensity parameter so as to bring the measured neural response intensity towards the target neural response intensity; extracting a representative value of stimulus intensity parameter corresponding to the target neural response intensity; and adjusting the target neural response intensity; repeat the capturing, processing, adjusting, extracting, and adjusting, yielding a plurality of (representative stimulus intensity, target response intensity) pairs; and estimating a baseline value of each of one or more physiological characteristics of the tissue from the plurality of (representative stimulus intensity, target response intensity) pairs, wherein each physiological characteristic varies around the baseline value as a result of a posture wave.

Example 24. A neuromodulation system comprising: an implantable electrode array comprising a plurality of electrodes; a stimulus source configured to provide a stimulus to be delivered via one or more stimulus electrodes to tissue proximal to the implantable electrode array, the one or more stimulus electrodes being selected from the plurality of electrodes; measurement circuitry configured to process a signal sensed from the tissue via one or more sense electrodes, the sensed signal including a neural response evoked by the stimulus, the one or more sense electrodes being selected from the plurality of electrodes; and a processor configured to: process the signal from the measurement circuitry in order to measure an intensity of each evoked neural response; control the stimulus source to adjust, using a feedback parameter, an intensity of the provided stimulus so as to bring the measured neural response intensity towards a target response intensity; measure a variation in the measured neural response intensity; and obtain a baseline estimate of a physiological characteristic from the measured variation in the neural response intensity, wherein the physiological characteristic varies around a baseline value as a result of a posture wave.

Example 25. The neuromodulation system of example 24, wherein the processor is configured to perturb the stimulus intensity periodically at a frequency higher than that of the posture wave.

Example 26. The neuromodulation system of example 25, wherein the processor is configured to perturb the stimulus intensity at half a frequency of the stimulus.

Example 27. The neuromodulation system of example 25, wherein the processor is configured to obtain the baseline estimate by: measuring a gain from an amplitude of the stimulus intensity perturbation to an amplitude of the variation in the measured neural response intensity; and obtaining the baseline estimate from the measured gain and the feedback parameter.

Example 28. The neuromodulation system of example 24, wherein the processor is configured to perturb the stimulus intensity by a step.

Example 29. The neuromodulation system of example 28, wherein the processor is configured to obtain the baseline estimate from a transient response of the measured neural response intensity and the feedback parameter.

Example 30. The neuromodulation system of example 24, wherein the processor is further configured to: measure an amplitude of variation in the measured neural response intensity at the original value of the feedback parameter; adjust the feedback parameter from an original value to zero; and measure an amplitude of variation in the measured neural response intensity at the zero value of the feedback parameter.

Example 31. The neuromodulation system of example 30, wherein the processor is configured to obtain the baseline estimate by: computing an attenuation in the amplitude of variation in the measured neural response intensity between the zero value of the feedback parameter and the original value of the feedback parameter; and obtain the baseline estimate from the attenuation and the original value of the feedback parameter.

Example 32. The neuromodulation system of example 31, wherein the processor is further configured to compute a range of variation of the physiological characteristic from the baseline estimate and the target response intensity.

Example 33. The neuromodulation system of any one of examples 24 to 32, further comprising an external computing device configured to communicate with a controller that is co-located with, and in communication with, the measurement circuitry and the stimulus source within an implantable electronics module.

Example 34. The neuromodulation system of example 33, wherein the processor is part of the external computing device and is configured by program instructions stored in an instruction memory of the external computing device.

Example 35. The neuromodulation system of any one of examples 24 to 34, wherein the processor is further configured to adjust the feedback parameter based on the baseline estimate of the physiological characteristic.

Example 36. A method of estimating a baseline value of one or more physiological characteristics of a patient, the method comprising: delivering a stimulus from one or more stimulus electrodes to tissue proximal to the stimulus electrodes, the one or more stimulus electrodes being selected from a plurality of electrodes of an implantable electrode array; sensing via one or more sense electrodes a signal from the tissue, the sensed signal including a neural response evoked by the stimulus, the one or more sense electrodes being selected from the plurality of electrodes; processing the sensed signal in order to measure an intensity of the evoked neural response; controlling a stimulus source to adjust, using a feedback parameter, an intensity of the delivered stimulus so as to bring the measured neural response intensity towards a target response intensity; measure a variation in the measured neural response intensity; and obtain a baseline estimate of a physiological characteristic from the measured variation in the neural response intensity, wherein the physiological characteristic varies around a baseline value as a result of a posture wave.

Example 37. A non-transitory computer readable medium for estimating a baseline value of one or more physiological characteristics of a patient, the medium comprising instructions which, when executed by one or more processors, causes performance of the following: delivering a stimulus from one or more stimulus electrodes to tissue proximal to the stimulus electrodes, the one or more stimulus electrodes being selected from a plurality of electrodes of an implantable electrode array; sensing via one or more sense electrodes a signal from the tissue, the sensed signal including a neural response evoked by the stimulus, the one or more sense electrodes being selected from the plurality of electrodes; processing the sensed signal in order to measure an intensity of the evoked neural response; controlling the stimulus source to adjust, using a feedback parameter, an intensity of the provided stimulus so as to bring the measured neural response intensity towards a target response intensity; measure a variation in the measured neural response intensity; and obtain a baseline estimate of a physiological characteristic from the measured variation in the neural response intensity, wherein the physiological characteristic varies around a baseline value as a result of a posture wave.

References herein to estimation, determination, comparison and the like are to be understood as referring to an automated process carried out on data by a processor operating to execute a predefined procedure suitable to effect the described estimation, determination and/or comparison step (s). The technology disclosed herein may be implemented in hardware (e.g., using digital signal processors, application specific integrated circuits (ASICs) or field programmable gate arrays (FPGAs)), or in software (e.g., using instructions tangibly stored on non-transitory computer-readable media for causing a data processing system to perform the steps described herein), or in a combination of hardware and software. The disclosed technology can also be embodied as computer-readable code on a computer-readable medium. The computer-readable medium can include any data storage device that can store data which can thereafter be read by a computer system. Examples of the computer-readable medium include read-only memory ("ROM"), random-access memory ("RAM"), magnetic tape, optical data storage devices, flash storage devices, or any other suitable storage devices. The computer-readable medium can also be distributed over network-coupled computer systems so that the computer-readable code is stored and/or executed in a distributed fashion.

BRIEF DESCRIPTION OF THE DRAWINGS

One or more implementations of the invention will now be described with reference to the accompanying drawings, in which:

FIG. 18 contains a flow chart illustrating a method 1800 of estimating a baseline value of one or more physiological characteristics of a patient according to one implementation of the present technology.

DETAILED DESCRIPTION OF THE PRESENT TECHNOLOGY

Figure 1:
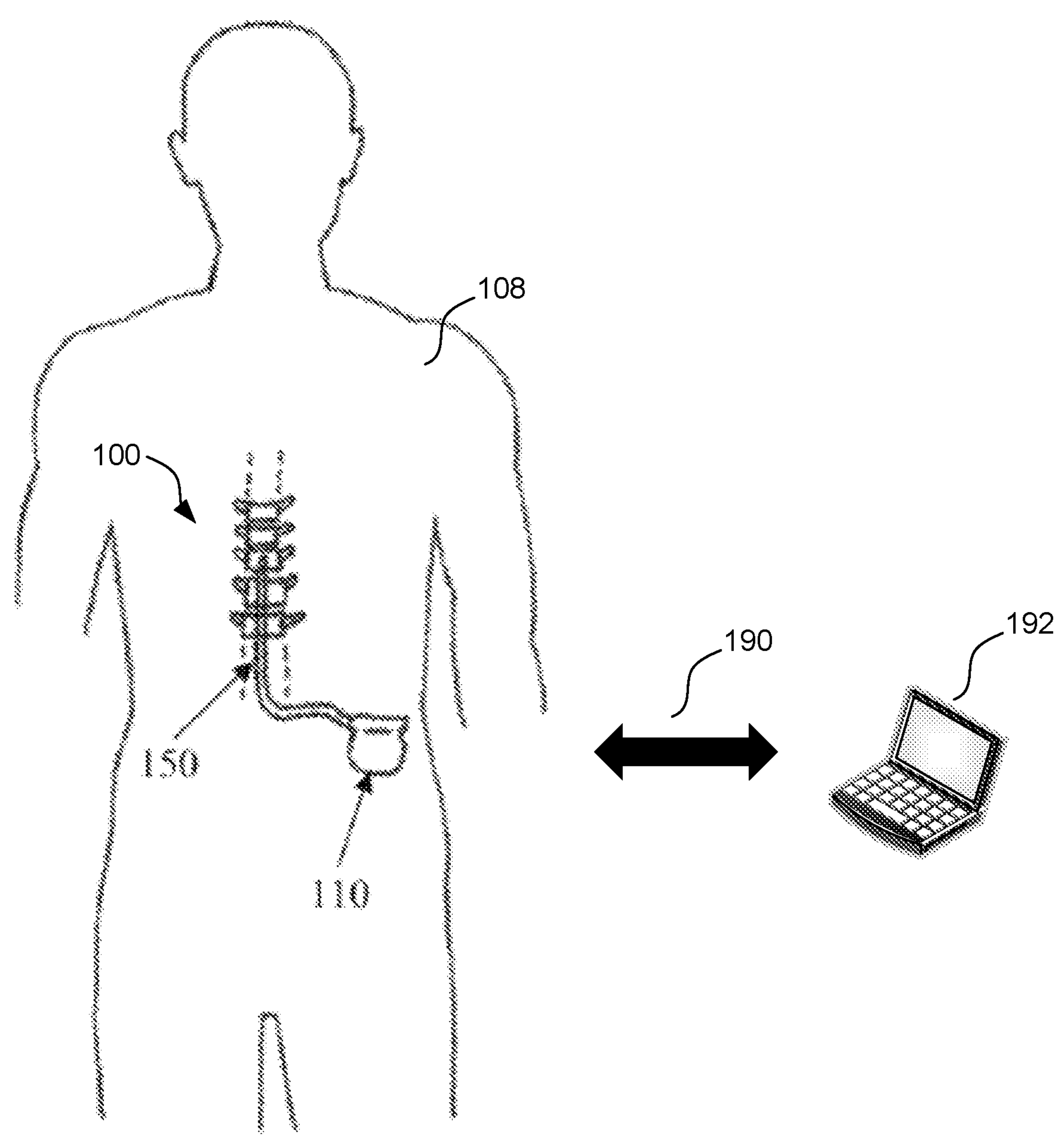
FIG. 1 schematically illustrates an implanted spinal cord stimulator, according to one implementation of the present technology.

FIG. 1 schematically illustrates an implanted spinal cord stimulator 100 in a patient 108, according to one implementation of the present technology. Stimulator 100 comprises an electronics module 110 implanted at a suitable location. In one implementation, stimulator 100 is implanted in the patient's lower abdominal area or posterior superior gluteal region. In other implementations, the electronics module 110 is implanted in other locations, such as a flank or subclavicular. Stimulator 100 further comprises an electrode array 150 implanted within the epidural space and connected to the module 110 by a suitable lead. The electrode array 150 may comprise one or more electrodes such as electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for stimulation and measurement. The electrodes may pierce or affix directly to the tissue itself.

Numerous aspects of the operation of implanted stimulator 100 may be programmable by an external computing device 192, which may be operable by a user such as a clinician or the patient 108. Moreover, implanted stimulator 100 serves a data gathering role, with gathered data being communicated to external device 192 via a transcutaneous communications channel 190. Communications channel 190 may be active on a substantially continuous basis, at periodic intervals, at non-periodic intervals, or upon request from the external device 192. External device 192 may thus provide a clinical interface configured to program the implanted stimulator 100 and recover data stored on the implanted stimulator 100. This configuration is achieved by program instructions collectively referred to as the Clinical Programming Application (CPA) and stored in an instruction memory of the clinical interface.

Figure 2:
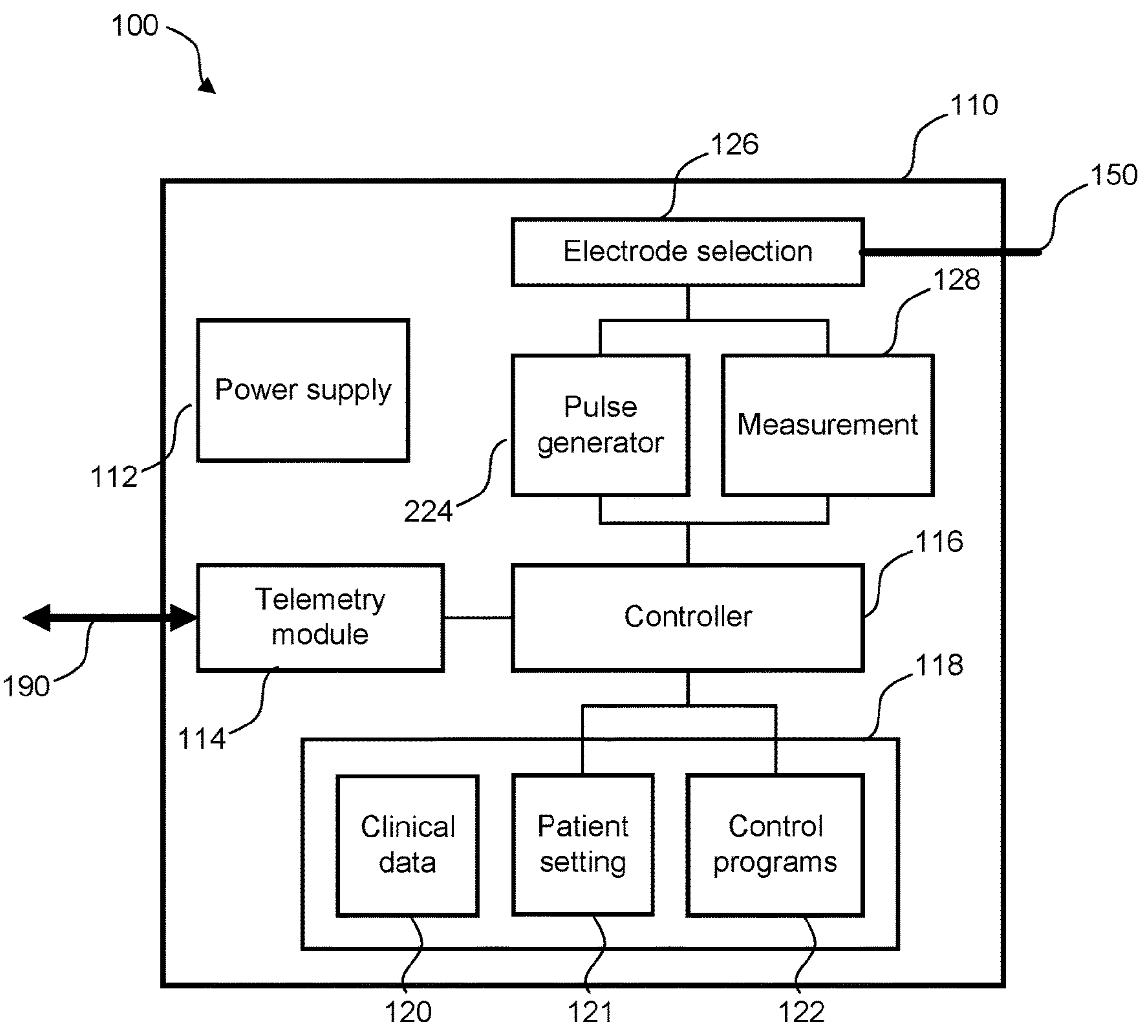
FIG. 2 is a block diagram of the stimulator of FIG. 1.

FIG. 2 is a block diagram of the stimulator 100. Electronics module 110 contains a battery 112 and a telemetry module 114. In implementations of the present technology, any suitable type of transcutaneous communications channel 190, such as infrared (IR), radiofrequency (RF), capacitive and inductive transfer, may be used by telemetry module 114 to transfer power and/or data to and from the electronics module 110 via communications channel 190. Module controller 116 has an associated memory 118 storing one or more of clinical data 120, clinical settings 121, control programs 122, and the like. Controller 116 is configured by control programs 122, sometimes referred to as firmware, to control a pulse generator 124 to generate stimuli, such as in the form of electrical pulses, in accordance with the clinical settings 121. Electrode selection module 126 switches the generated pulses to the selected electrode(s) of electrode array 150, for delivery of the pulses to the tissue surrounding the selected electrode(s). Measurement circuitry 128, which may comprise an amplifier and/or an analog-to-digital converter (ADC), is configured to process signals comprising neural responses sensed at measurement electrode(s) of the electrode array 150 as selected by electrode selection module 126.

Figure 3:
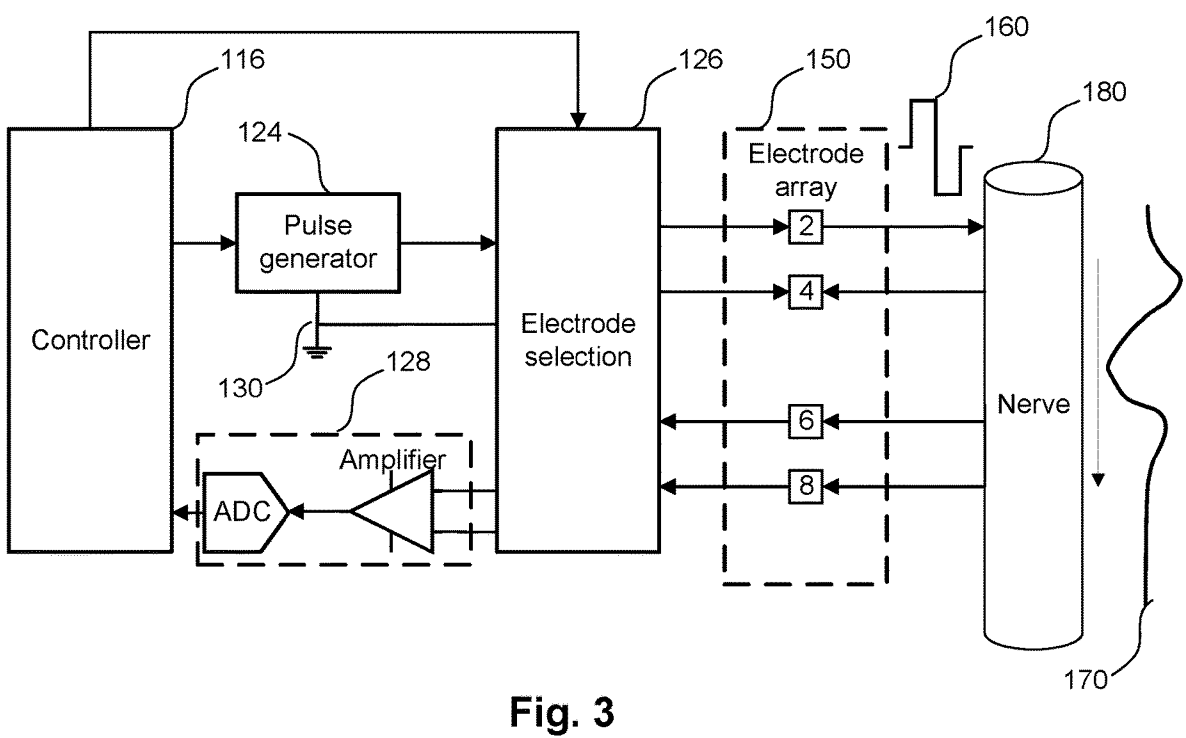
FIG. 3 is a schematic illustrating interaction of the implanted stimulator of FIG. 1 with a nerve.

FIG. 3 is a schematic illustrating interaction of the implanted stimulator 100 with a nerve 180 in the patient 108. In the implementation illustrated in FIG. 3 the nerve 180 may be located in the spinal cord, however in alternative implementations the stimulator 100 may be positioned adjacent any desired neural tissue including a peripheral nerve, visceral nerve, parasympathetic nerve or a brain structure. Electrode selection module 126 selects a stimulus electrode 2 of electrode array 150 through which to deliver a pulse from the pulse generator 124 to surrounding tissue including nerve 180. A pulse may comprise one or more phases, e.g. a biphasic stimulus pulse 160 comprises two phases. Electrode selection module 126 also selects a return electrode 4 of the electrode array 150 for stimulus charge recovery in each phase, to maintain a zero net charge transfer. Because a given electrode may act as both a stimulus and a return electrode over a complete multiphasic stimulus pulse, both electrodes are generally referred to as stimulus electrodes. The use of two electrodes in this manner for delivering and recovering current in each stimulus phase is referred to as bipolar stimulation. Alternative embodiments may apply other forms of bipolar stimulation, or may use a greater number of stimulus electrodes. The set of stimulus electrodes and their respective polarities is referred to as the stimulus electrode configuration. Electrode selection module 126 is illustrated as connecting to a ground 130 of the pulse generator 124 to enable stimulus charge recovery via the return electrode 4. However, other connections for charge recovery may be used in other implementations.

Delivery of an appropriate stimulus from stimulus electrodes 2 and 4 to the nerve 180 evokes a neural response 170 comprising an evoked compound action potential (ECAP) which will propagate along the nerve 180 as illustrated at a rate known as the conduction velocity. The ECAP may be evoked for therapeutic purposes, which in the case of a spinal cord stimulator for chronic pain may be to create paraesthesia at a desired location. To this end, the stimulus electrodes 2 and 4 are used to deliver stimuli periodically at any therapeutically suitable frequency, for example 30 Hz, although other frequencies may be used including frequencies as high as the kHz range. In alternative implementations, stimuli may be delivered in a non-periodic manner such as in bursts, or sporadically, as appropriate for the patient 108. To program the stimulator 100 to the patient 108, a clinician may cause the stimulator 100 to deliver stimuli of various configurations which seek to produce a sensation that is experienced by the user as paraesthesia. When a stimulus configuration is found which evokes paraesthesia in a location and of a size which is congruent with the area of the patient's body affected by pain and of a quality that is comfortable for the patient, the clinician or the patient nominates that configuration for ongoing use. The program parameters may be loaded into the memory 118 of the stimulator 100 as the clinical settings 121.

Figure 6:
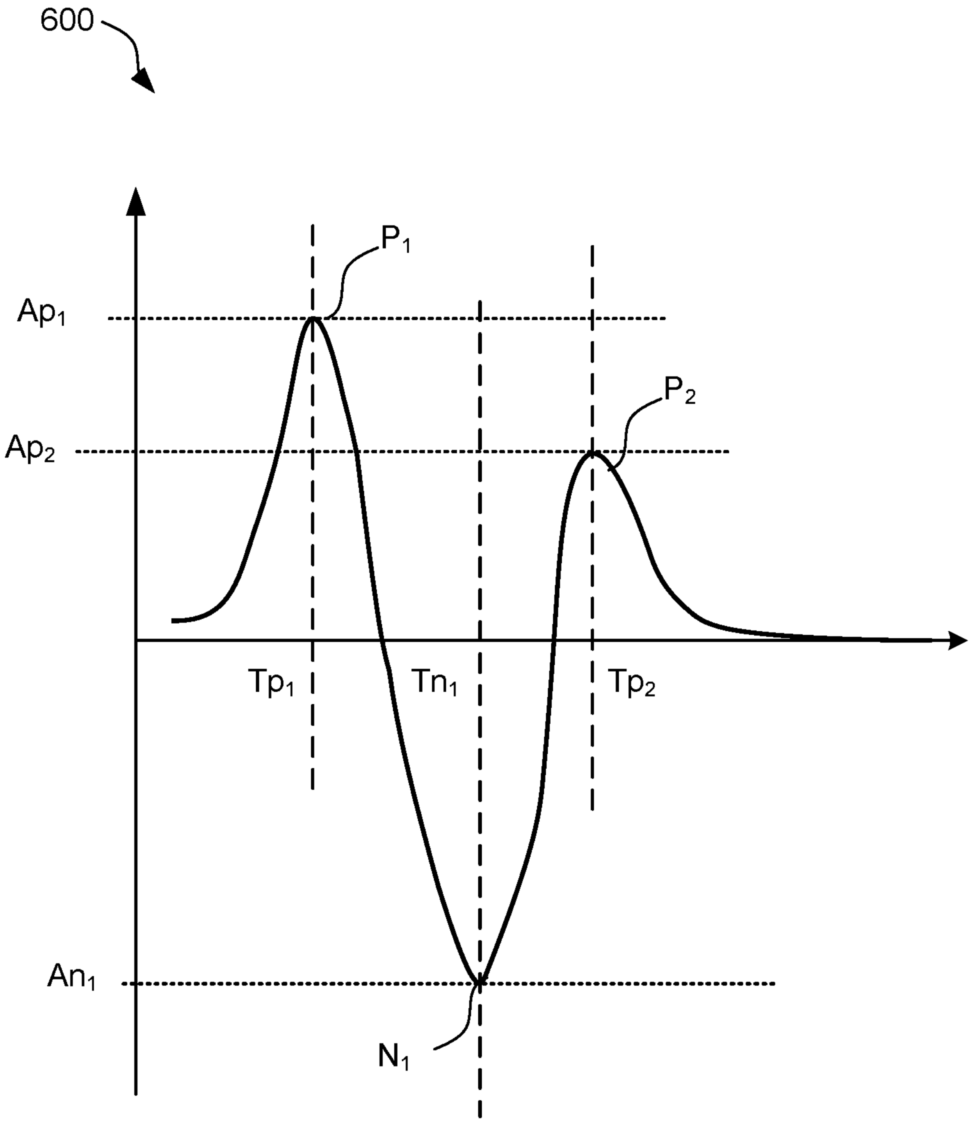
FIG. 6 illustrates the typical form of an electrically evoked compound action potential (ECAP) of a healthy subject.

FIG. 6 illustrates the typical form of an ECAP 600 of a healthy subject, as recorded at a single measurement electrode referenced to the system ground 130. The shape and duration of the single-ended ECAP 600 shown in FIG. 6 is predictable because it is a result of the ion currents produced by the ensemble of fibres depolarising and generating action potentials (APs) in response to stimulation. The evoked action potentials (EAPs) generated synchronously among a large number of fibres sum to form the ECAP 600. The ECAP 600 generated from the synchronous depolarisation of a group of similar fibres comprises a positive peak P1, then a negative peak N1, followed by a second positive peak P2. This shape is caused by the region of activation passing the measurement electrode as the action potentials propagate along the individual fibres.

The ECAP may be recorded differentially using two measurement electrodes, as illustrated in FIG. 3. Differential ECAP measurements are less subject to common-mode noise on the surrounding tissue than single-ended ECAP measurements. Depending on the polarity of recording, a differential ECAP may take an inverse form to that shown in FIG. 6, i.e. a form having two negative peaks N1 and N2, and one positive peak P1. Alternatively, depending on the distance between the two measurement electrodes, a differential ECAP may resemble the time derivative of the ECAP 600, or more generally the difference between the ECAP 600 and a time-delayed copy thereof.

The ECAP 600 may be parametrised by any suitable parameter(s) of which some are indicated in FIG. 6. The amplitude of the positive peak P1 is Ap1 and occurs at time Tp1. The amplitude of the positive peak P2 is Ap2 and occurs at time Tp2. The amplitude of the negative peak P1 is An1 and occurs at time Tn1. The peak-to-peak amplitude is Ap1+An1. A recorded ECAP will typically have a maximum peak-to-peak amplitude in the range of microvolts and a duration of 2 to 3 ms.

The stimulator 100 is further configured to detect the existence and measure the intensity of ECAPs 170 propagating along nerve 180, whether such ECAPs are evoked by the stimulus from electrodes 2 and 4, or otherwise evoked. To this end, any electrodes of the array 150 may be selected by the electrode selection module 126 to serve as recording electrode 6 and reference electrode 8, whereby the electrode selection module 126 selectively connects the chosen electrodes to the inputs of the measurement circuitry 128. Thus, signals sensed by the measurement electrodes 6 and 8 subsequent to the respective stimuli are passed to the measurement circuitry 128, which may comprise a differential amplifier and an analog-to-digital converter (ADC), as illustrated in FIG. 3. The recording electrode and the reference electrode are referred to as the measurement electrode configuration. The measurement circuitry 128 for example may operate in accordance with the teachings of the above-mentioned International Patent Publication No. WO 2012/155183.

Signals sensed by the measurement electrodes 6, 8 and processed by measurement circuitry 128 are further processed by an ECAP detector implemented within controller 116, configured by control programs 122, to obtain information regarding the effect of the applied stimulus upon the nerve 180. In some implementations, the sensed signals are processed by the ECAP detector in a manner which extracts and stores one or more parameters from each evoked neural response or group of evoked neural responses contained in the sensed signal. In one such implementation, the parameter comprises a peak-to-peak ECAP amplitude in microvolts (μV). For example, the neural responses may be processed by the ECAP detector to determine the peak-to-peak ECAP amplitude in accordance with the teachings of International Patent Publication No. WO 2015/074121, the contents of which are incorporated herein by reference. Alternative implementations of the ECAP detector may extract and store an alternative parameter from the neural response, or may extract and store two or more parameters from the neural response.

Stimulator 100 applies stimuli over a potentially long period such as days, weeks, or months and during this time may store parameters of neural responses, clinical settings, paraesthesia target level, and other operational parameters in memory 118. To effect suitable SCS therapy, stimulator 100 may deliver tens, hundreds or even thousands of stimuli per second, for many hours each day. Each neural response or group of responses generates one or more parameters such as a measure of the amplitude of the neural response. Stimulator 100 thus may produce such data at a rate of tens or hundreds of Hz, or even kHz, and over the course of hours or days this process results in large amounts of clinical data 120 which may be stored in the memory 118. Memory 118 is however necessarily of limited capacity and care is thus required to select compact data forms for storage into the memory 118, to ensure that the memory 118 is not exhausted before such time that the data is expected to be retrieved wirelessly by external device 192, which may occur only once or twice a day, or less.

Figure 4A:
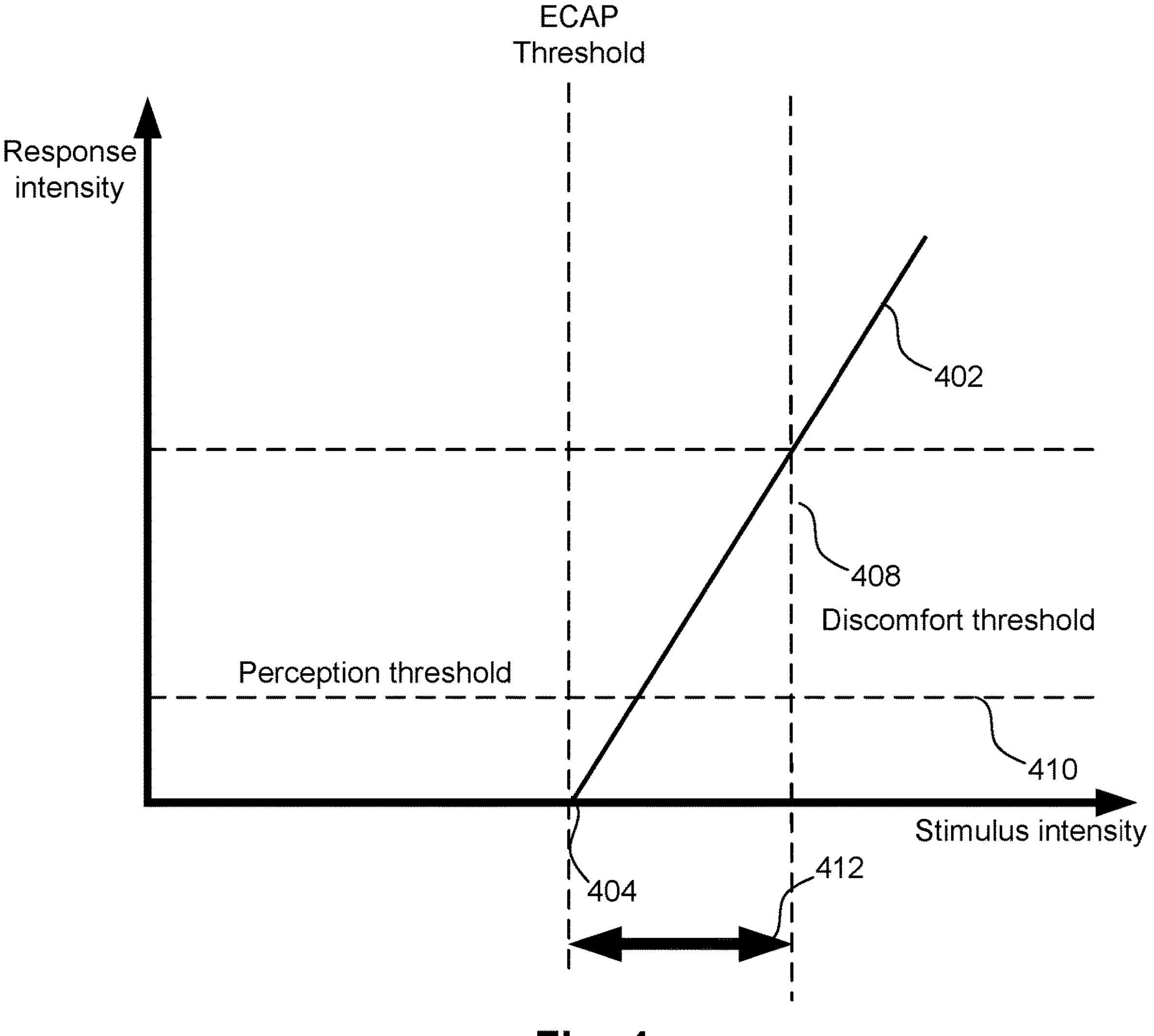
FIG. 4*a* illustrates an idealised activation plot for one posture of a patient undergoing neural stimulation.

An activation plot, or growth curve, is an approximation to the relationship between stimulus intensity (e.g. an amplitude of the current pulse 160) and intensity of neural response 170 evoked by the stimulus (e.g. an ECAP amplitude). FIG. 4*a* illustrates an idealised activation plot 402 for one posture of the patient 108. The activation plot 402 shows a linearly increasing ECAP amplitude for stimulus intensity values above a threshold 404 referred to as the ECAP threshold. The ECAP threshold exists because of the binary nature of fibre recruitment; if the field strength is too low, no fibres will be recruited. However, once the field strength exceeds a threshold, fibres begin to be recruited, and their individual evoked action potentials are independent of the strength of the field. The ECAP threshold 404 therefore reflects the field strength at which significant numbers of fibres begin to be recruited, and the increase in response intensity with stimulus intensity above the ECAP threshold reflects increasing numbers of fibres being recruited. Below the ECAP threshold 404, the ECAP amplitude may be taken to be zero. Above the ECAP threshold 404, the activation plot 402 has a positive, approximately constant slope indicating a linear relationship between stimulus intensity and the ECAP amplitude. Such a relationship may be modelled as:

$$y = \begin{cases} S(s-T), & s \geq T \\ 0, & s < T \end{cases} \tag{1}$$

where s is the stimulus intensity, y is the ECAP amplitude, T is the ECAP threshold and S is the slope of the activation plot (referred to herein as the patient sensitivity). The slope S and the ECAP threshold T are the key parameters of the activation plot 402.

FIG. 4*a* also illustrates a discomfort threshold 408, which is a stimulus intensity above which the patient 108 experiences uncomfortable or painful stimulation. FIG. 4*a* also illustrates a perception threshold 410. The perception threshold 410 corresponds to an ECAP amplitude that is perceivable by the patient. There are a number of factors which can influence the position of the perception threshold 410, including the posture of the patient. Perception threshold 410 may correspond to a stimulus intensity that is greater than the ECAP threshold 404, as illustrated in FIG. 4*a*, if patient 108 does not perceive low levels of neural activation. Conversely, the perception threshold 410 may correspond to a stimulus intensity that is less than the ECAP threshold 404, if the patient has a high perception sensitivity to lower levels of neural activation than can be detected in an ECAP, or if the signal to noise ratio of the ECAP is low.

For effective and comfortable operation of an implantable neuromodulation device such as the stimulator 100, it is desirable to maintain stimulus intensity within a therapeutic range. A stimulus intensity within a therapeutic range 412 is above the ECAP threshold 404 and below the discomfort threshold 408. In principle, it would be straightforward to measure these limits and ensure that stimulus intensity, which may be closely controlled, always falls within the therapeutic range 412. However, the activation plot, and therefore the therapeutic range 412, varies with the posture of the patient 108.

Figure 4B:
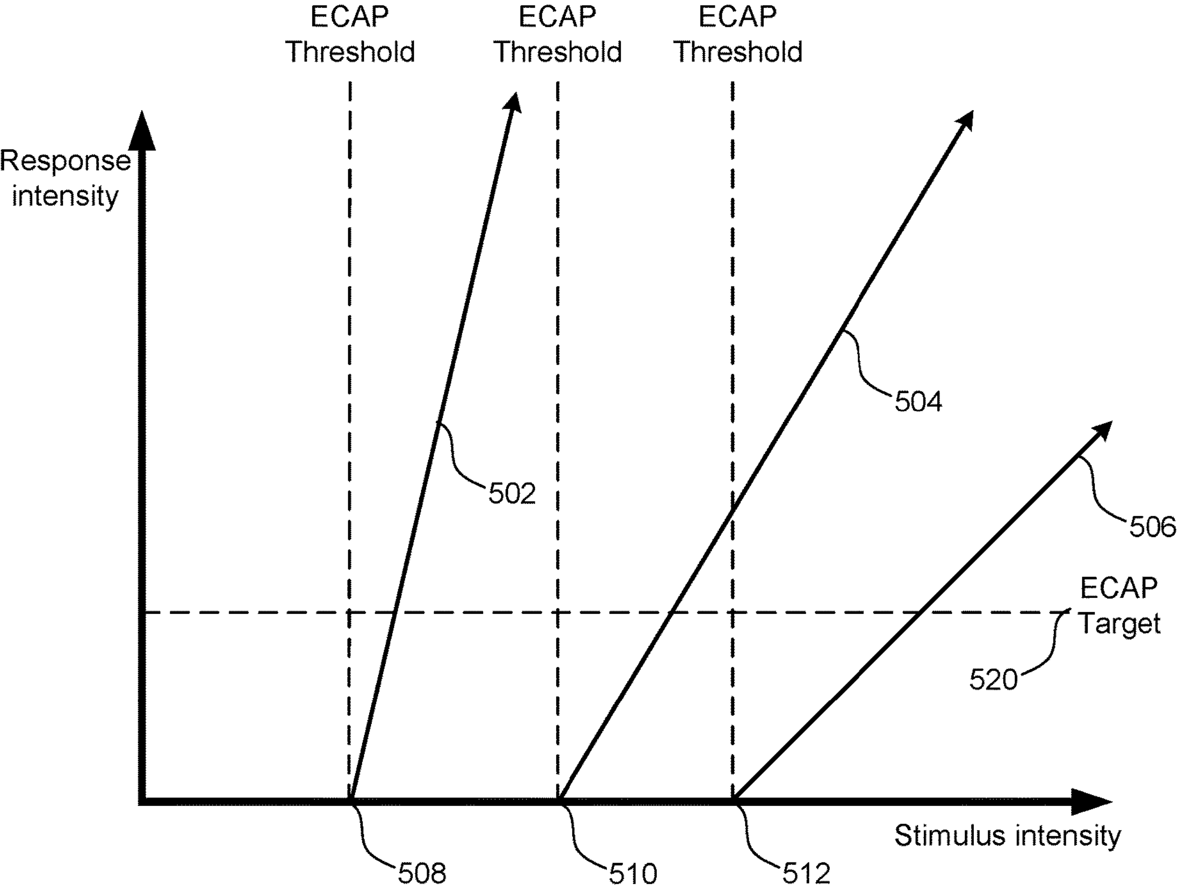
FIG. 4*b* illustrates the variation in the activation plots with changing posture of the patient.

FIG. 4*b* illustrates the variation in the activation plots with changing posture of the patient. A change in posture of the patient may cause a change in impedance of the electrode-tissue interface or a change in the distance between electrodes and the neurons. While the activation plots for only three postures, 502, 504 and 506, are shown in FIG. 4*b*, the activation plot for any given posture can lie between or outside the activation plots shown, on a continuously varying basis depending on posture. Consequently, as the patient's posture changes, the ECAP threshold changes, as indicated by the ECAP thresholds 508, 510, and 512 for the respective activation plots 502, 504, and 506. Additionally, as the patient's posture changes, the slope of the activation plot also changes, as indicated by the varying slopes of activation plots 502, 504, and 506. In general, as the distance between the stimulus electrodes and the spinal cord increases, the ECAP threshold increases and the slope of the activation plot decreases. The activation plots 502, 504, and 506 therefore correspond to increasing distance between stimulus electrodes and spinal cord, and decreasing patient sensitivity.

To keep the applied stimulus intensity within the therapeutic range as patient posture varies, in some implementations an implantable neuromodulation device such as the stimulator 100 may adjust the applied stimulus intensity based on a feedback variable that is determined from one or more extracted ECAP parameters. In one implementation, the device may adjust the stimulus intensity to maintain the extracted ECAP amplitude at a target response intensity. For example, the device may calculate an error between a target ECAP amplitude and a measured ECAP amplitude, and adjust the applied stimulus intensity to reduce the error as much as possible, such as by adding the scaled error to the current stimulus intensity. A neuromodulation device that operates by adjusting the applied stimulus intensity based on an extracted ECAP parameter is said to be operating in closed-loop mode and will also be referred to as a closed-loop neural stimulation (CLNS) device. By adjusting the applied stimulus intensity to maintain the extracted ECAP amplitude at an appropriate target response intensity, such as an ECAP target 520 illustrated in FIG. 4*b*, a CLNS device will generally keep the stimulus intensity within the therapeutic range as patient posture varies.

A CLNS device comprises a stimulator that takes a stimulus intensity value and converts it into a neural stimulus comprising a sequence of electrical pulses according to a predefined stimulation pattern. The stimulation pattern is characterised by multiple parameters including stimulus amplitude, pulse width, number of phases, order of phases, number of stimulus electrode poles (two for bipolar, three for tripolar etc.), and stimulus rate or frequency. At least one of the stimulus parameters, for example the stimulus amplitude, is controlled by the feedback loop.

In an example CLNS system, a user (e.g. the patient or a clinician) sets a target response intensity, and the CLNS device performs proportional-integral-differential (PID) control. In some implementations, the differential contribution is disregarded and the CLNS device uses a first order integrating feedback loop. The stimulator produces stimulus in accordance with a stimulus intensity parameter, which evokes a neural response in the patient. The evoked neural response (e.g. an ECAP) is detected, and its amplitude measured by the CLNS device and compared to the target response intensity.

The measured neural response amplitude, and its deviation from the target response intensity, is used by the feedback loop to determine possible adjustments to the stimulus intensity parameter to maintain the neural response at the target intensity. If the target intensity is properly chosen, the patient receives consistently comfortable and therapeutic stimulation through posture changes and other perturbations to the stimulus/response behaviour.

Figure 5:
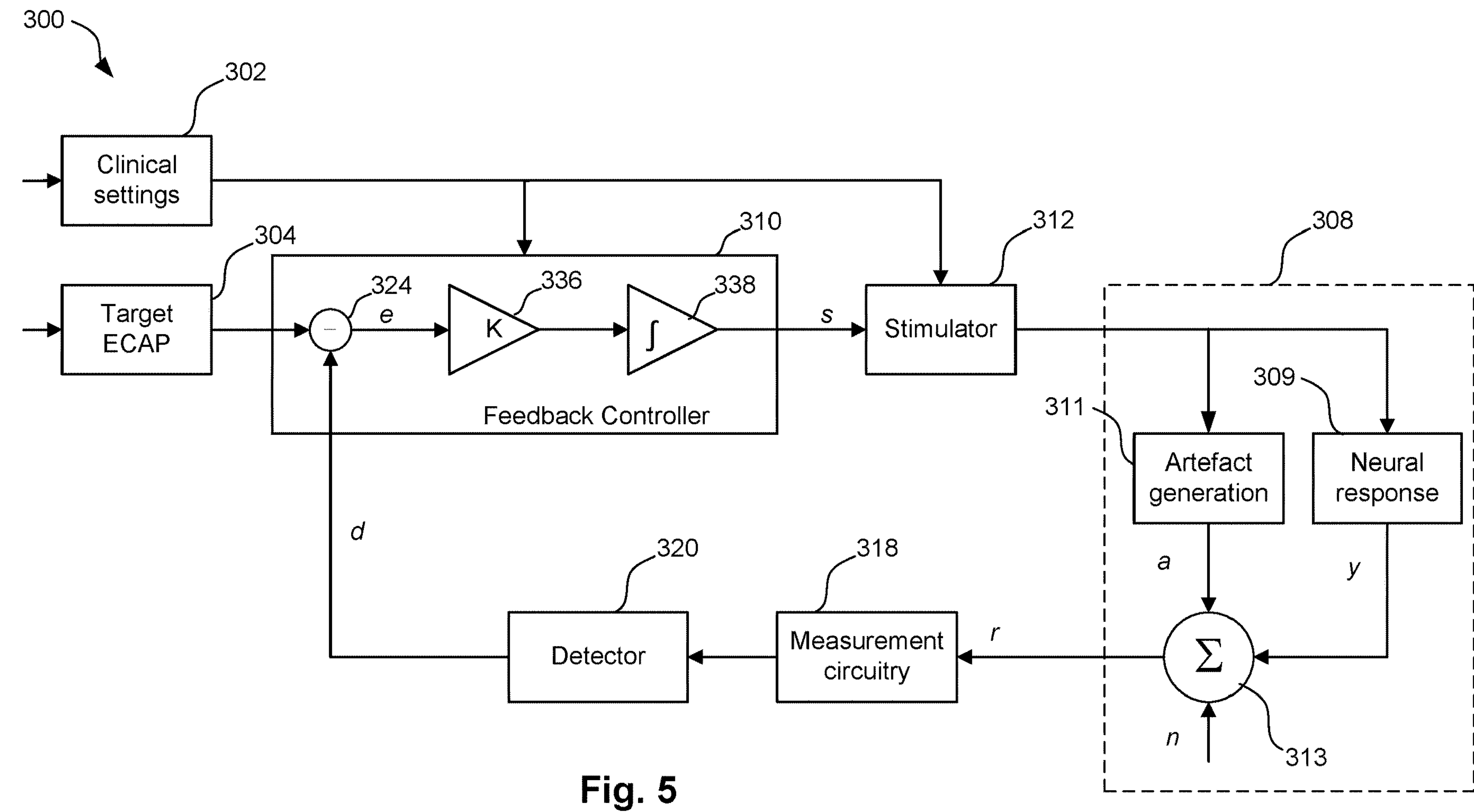
FIG. 5 is a schematic illustrating elements and inputs of a closed-loop neural stimulation system, according to one implementation of the present technology.

FIG. 5 is a schematic illustrating elements and inputs of a closed-loop neural stimulation (CLNS) system 300, according to one implementation of the present technology. The system 300 comprises a stimulator 312 which converts a stimulus intensity parameter (for example a stimulus current amplitude) s, in accordance with a set of predefined stimulus parameters, to a neural stimulus comprising a sequence of electrical pulses on the stimulus electrodes (not shown in FIG. 5). According to one implementation, the predefined stimulus parameters comprise the number and order of phases, the number of stimulus electrode poles, the pulse width, and the stimulus rate or frequency.

The generated stimulus crosses from the electrodes to the spinal cord, which is represented in FIG. 5 by the dashed box 308. The box 309 represents the evocation of a neural response y by the stimulus as described above. The box 311 represents the evocation of an artefact signal a, which is dependent on stimulus intensity and other stimulus parameters, as well as the electrical environment of the measurement electrodes. Various sources of noise n, as well as the artefact a, may add to the evoked response y at the summing element 313 to form the sensed signal r, including: electrical noise from external sources such as 50 Hz mains power; electrical disturbances produced by the body such as neural responses evoked not by the device but by other causes such as peripheral sensory input; EEG; EMG; and electrical noise from measurement circuitry 318.

The neural recruitment arising from the stimulus is affected by mechanical changes, including posture changes, walking, breathing, heartbeat and so on. Mechanical changes may cause impedance changes, or changes in the location and orientation of the nerve fibres relative to the electrode array(s). As described above, the intensity of the evoked response provides a measure of the recruitment of the fibres being stimulated. In general, the more intense the stimulus, the more recruitment and the more intense the evoked response. An evoked response typically has a maximum amplitude in the range of microvolts, whereas the voltage resulting from the stimulus applied to evoke the response is typically several volts.

Measurement circuitry 318, which may be identified with measurement circuitry 128, amplifies the sensed signal r (including evoked neural response, artefact, and noise), and samples the amplified sensed signal r to capture a "signal window" comprising a predetermined number of samples of the amplified sensed signal r. The ECAP detector 320 processes the signal window and outputs a measured neural response intensity d. In one implementation, the neural response intensity d comprises a peak-to-peak ECAP amplitude. The measured response intensity d is input into the feedback controller 310. The feedback controller 310 comprises a comparator 324 that compares the measured response intensity d to the target ECAP amplitude as set by the target ECAP controller 304 and provides an indication of the difference between the measured response intensity d and the target ECAP amplitude. This difference is the error value, e. The error value e is input into the feedback controller 310.

The feedback controller 310 calculates an adjusted stimulus intensity parameter, s, with the aim of maintaining a measured response intensity d equal to the target ECAP amplitude. Accordingly, the feedback controller 310 adjusts the stimulus intensity parameter s to minimise the error value, e. In one implementation, the controller 310 utilises a first order integrating function, using a gain element 336 and an integrator 338, in order to provide suitable adjustment to the stimulus intensity parameter s. According to such an implementation, the current stimulus intensity parameter s may be computed by the feedback controller 310 as $$s = \int Ke\,dt \quad (2)$$

where K is the gain of the gain element 336 (the controller gain). This relation may also be represented as $$\delta s = Ke \quad (3)$$

where δs is an adjustment to the current stimulus intensity parameter s.

A target ECAP amplitude is input to the feedback controller 310 via the target ECAP controller 304. In one embodiment, the target ECAP controller 304 provides an indication of a specific target ECAP amplitude. In another embodiment, the target ECAP controller 304 provides an indication to increase or to decrease the present target ECAP amplitude. The target ECAP controller 304 may comprise an input into the CLNS system 300, via which the patient or clinician can input a target ECAP amplitude, or indication thereof. The target ECAP controller 304 may comprise memory in which the target ECAP amplitude is stored, and provided to the feedback controller 310.

A clinical settings controller 302 provides clinical settings to the system 300, including the feedback controller 310 and the stimulus parameters for the stimulator 312 that are not under the control of the feedback controller 310. In one example, the clinical settings controller 302 may be configured to adjust the controller gain K of the feedback controller 310 to adapt the feedback loop to patient sensitivity. The clinical settings controller 302 may comprise an input into the CLNS system 300, via which the patient or clinician can adjust the clinical settings. The clinical settings controller 302 may comprise memory in which the clinical settings are stored, and are provided to components of the system 300.

In some implementations, two clocks (not shown) are used, being a stimulus clock operating at the stimulus frequency (e.g. 60 Hz) and a sample clock for sampling the sensed signal r (for example, operating at a sampling frequency of 10 kHz). As the ECAP detector 320 is linear, only the stimulus clock affects the dynamics of the CLNS system 300. On the next stimulus clock cycle, the stimulator 312 outputs a stimulus in accordance with the adjusted stimulus intensity s. Accordingly, there is a delay of one stimulus clock cycle before the stimulus intensity is updated in light of the error value e.

Figure 7:
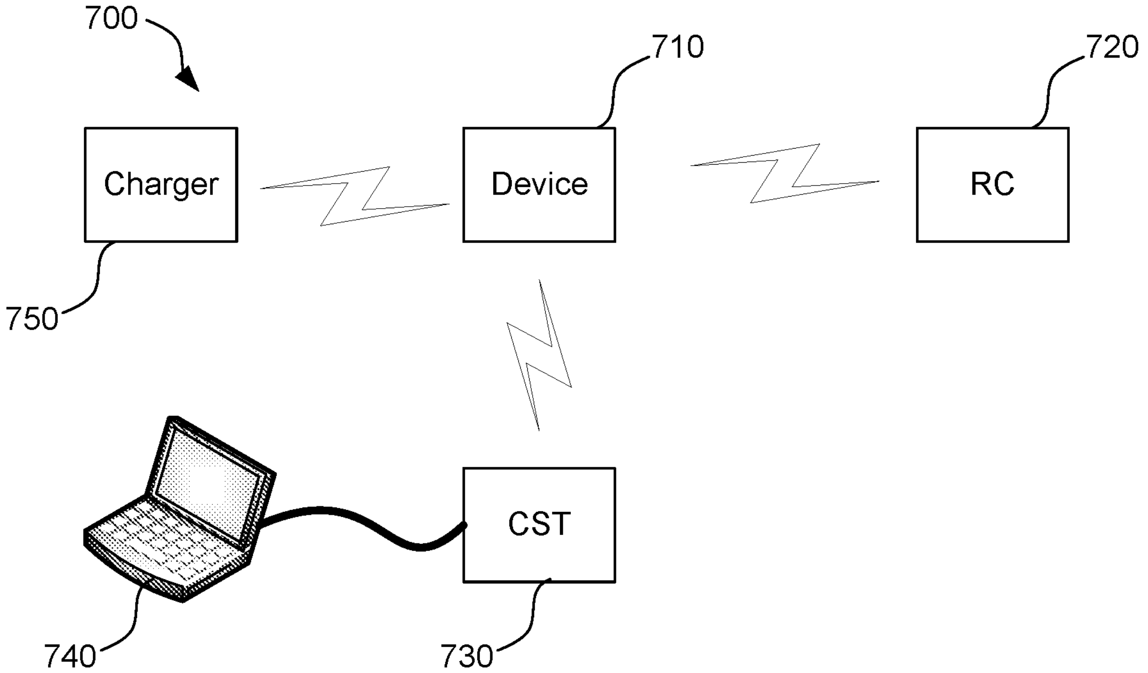
FIG. 7 is a block diagram of a neuromodulation therapy system including the implanted stimulator of FIG. 1 according to one implementation of the present technology.

FIG. 7 is a block diagram of a neuromodulation system 700. The neuromodulation system 700 is centered on a neuromodulation device 710. In one example, the neuromodulation device 710 may be implemented as the stimulator 100 of FIG. 1, implanted within a patient (not shown). The neuromodulation device 710 is connected wirelessly to a remote controller (RC) 720. The remote controller 720 is a portable computing device that provides the patient with control of their stimulation in the home environment by allowing control of the functionality of the neuromodulation device 710, including one or more of the following functions: enabling or disabling stimulation; adjustment of stimulus intensity or target neural response intensity; and selection of a stimulation control program from the control programs stored on the neuromodulation device 710.

The charger 750 is configured to recharge a rechargeable power source of the neuromodulation device 710. The recharging is illustrated as wireless in FIG. 7 but may be wired in alternative implementations.

The neuromodulation device 710 is wirelessly connected to a Clinical System Transceiver (CST) 730. The wireless connection may be implemented as the transcutaneous communications channel 190 of FIG. 1. The CST 730 acts as an intermediary between the neuromodulation device 710 and the Clinical Interface (CI) 740, to which the CST 730 is connected. A wired connection is shown in FIG. 7, but in other implementations, the connection between the CST 730 and the CI 740 is wireless.

The CI 740 may be implemented as the external computing device 192 of FIG. 1. The CI 740 is configured to program the neuromodulation device 710 and recover data stored on the neuromodulation device 710. This configuration is achieved by program instructions collectively referred to as the Clinical Programming Application (CPA) and stored in an instruction memory of the CI 740.

The Assisted Programming System

As mentioned above, obtaining patient feedback about their sensations is important during programming of closed-loop neural stimulation, but mediation by trained clinical engineers is expensive and time-consuming. It would therefore be advantageous if patients could program their own implantable device themselves. However, interfaces for current programming systems are non-intuitive and generally unsuitable for direct use by patients because of their technical nature. There is therefore a need for a CPA to be as intuitive for non-technical users as possible while avoiding discomfort to the patient. Implementations of an Assisted Programming System (APS) according to the present technology are generally configured to meet this need.

In some implementations, the APS comprises two elements: the Assisted Programming Module (APM), which forms part of the CPA, and the Assisted Programming Firmware (APF), which forms part of the control programs 122 executed by the controller 116 of the electronics module 110. The data obtained from the patient is analysed by the APM to determine the parameters and settings for the neural stimulation therapy to be delivered by the stimulator 100. The APF is configured to complement the operation of the APM by responding to commands issued by the APM via the CST 730 to the stimulator 100 to deliver specified stimuli to the patient, and by returning, via the CST 730, measurements of neural responses to the delivered stimuli.

In other implementations, all the processing of the APS according to the present technology is done by the APF. In other words, the data obtained from the patient is not passed to the APM, but is analysed by the controller 116 of the device 710, configured by the APF, to determine the parameters and settings for the neural stimulation therapy to be delivered by the stimulator 100.

In implementations of the APS in which the APM analyses the data from the patient, the APS instructs the device 710 to capture and return signal windows to the CI 740 via the CST 730. In such implementations, the device 710 captures the signal windows using the measurement circuit 128 and bypasses the ECAP detector 320, storing the data representing the raw signal windows temporarily in memory 118 before transmitting the data representing the captured signal windows to the APS. The signal window may for example comprise 164 samples of the sensed signal, sampled by the ADC at a sampling frequency of 16 kHz (and therefore of duration approximately 10 ms).

Following the programming, the APS may load the determined program onto the device 710 to govern subsequent neural stimulation therapy. In one implementation, the program comprises clinical settings 121, also referred to as therapy parameters, that are input to the neuromodulation device by, or stored in, the clinical settings controller 302. The patient may subsequently control the device 710 to deliver the therapy according to the determined program using the remote controller 720 as described above. The determined program may also, or alternatively, be loaded into the CPA for validation and modification.

Estimating Physiological Characteristics

The key relationship governing closed-loop SCS for a patient is that between stimulus intensity and neural response intensity, encapsulated in the activation plot, an example of which is illustrated in FIG. 4*a*. The parameters of the activation plot, as modelled in Equation (1), are ECAP threshold T and sensitivity S. These parameters are physiological characteristics of a patient that govern the choice of closed-loop SCS therapy parameters, as described below.

Figure 8A:
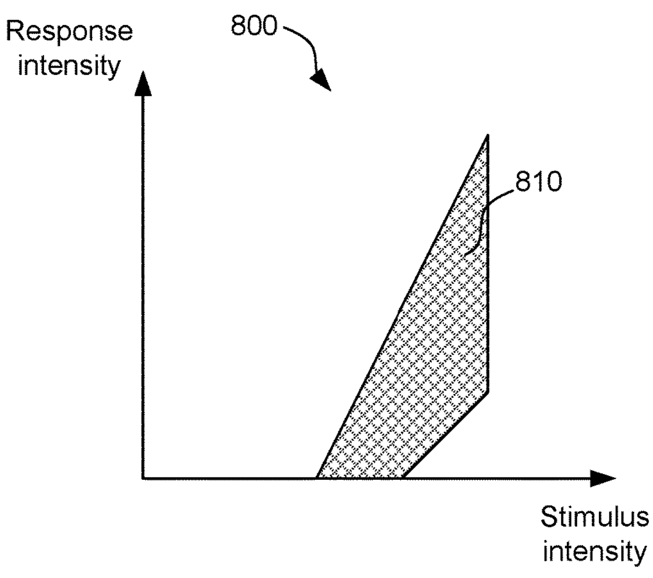
FIG. 8*a* is graph of neural response intensity vs stimulus intensity for a cervical patient.

As illustrated in FIG. 4*b*, the activation plot varies significantly with posture. For certain patients, the activation plot even varies significantly within a single posture as a result of cyclical anatomic events such as heartbeat and breathing, which perturb the distance between the electrode array and the spinal cord. Such cyclical anatomic perturbations may be referred to as "posture waves" as they mimic the effects of a periodic variation of posture. This is particularly likely for patients whose electrode array has been implanted near the cervical vertebrae, because of the greater mobility of the implanted electrode array in relation to cervical vertebrae compared to that of lower vertebrae during posture waves. FIG. 8*a* is a graph 800 of neural response intensity vs stimulus intensity for a cervical patient. The region 810 is the range within which plotted values of (stimulus intensity, response intensity) are likely to vary within a fixed posture, solely as a result of posture waves.

One method of estimating the patient's "baseline" ECAP threshold and sensitivity through a posture wave is to hold the stimulus intensity constant, so the neural response intensity fluctuates over the posture wave. A representative response intensity, such as an average value, may be extracted from the fluctuation of the response intensity to give a (stimulus intensity, representative response intensity) value pair, possibly along with a range of variation of the response intensity due to the posture wave. This may be repeated for a number of stimulus intensity values, giving a number of (stimulus intensity, representative response intensity) value pairs, each possibly accompanied by a range of variation of the response intensity. An activation plot of a predetermined form, such as piecewise linear as illustrated in FIG. 4*a*, may be fitted to the value pairs, and the patient's baseline values of ECAP threshold T and sensitivity S may be extracted from the fitted activation plot for the current posture. The fitting process may also calculate confidence intervals around the fitted values of T and S reflecting the size of their variations due to the posture wave. The result would be ranges of variation of each characteristic, bounded by the highest and lowest probable values that could be extracted from the fitted activation plot.

The baseline estimates of the patient's ECAP threshold T and sensitivity S and their respective ranges of variation may be used to initialise the parameters, such as the controller gain K, for a CLNS system such as the system 300 illustrated in FIG. 5. One implementation of the setting of CLNS system parameters such as the controller gain K based on the patient sensitivity S is described in Patent Cooperation Treaty Patent Publication no. WO 2016/090436, the entire contents of which are herein incorporated by reference. In one example, the controller gain K is set to a desired loop cutoff frequency, such as 3 Hz, divided by a value of patient sensitivity S at the maximum (most sensitive) value of its range.

Figure 8B:
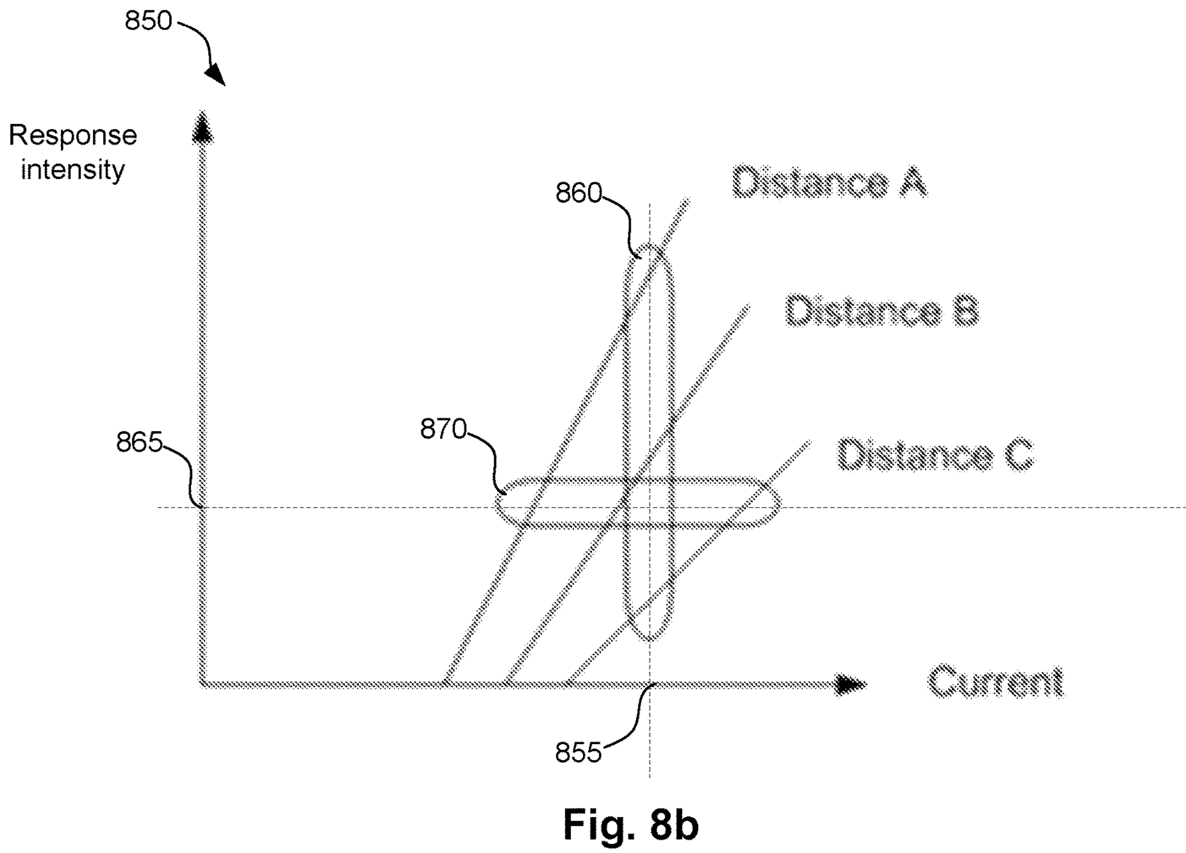
FIG. 8*b* is a graph containing three activation plots corresponding to different electrode-cord distances due to a posture wave in a fixed posture.

However, the above-described method may produce discomfort at certain points of the posture wave. FIG. 8*b* is a graph 850 containing three activation plots corresponding to different electrode-cord distances, labelled Distance A, Distance B, and Distance C, due to a posture wave in a fixed posture. If the activation plot is measured in the constant-stimulus manner described above, the response intensity at the stimulus intensity 855 varies within the locus 860. It might be that for points at the top of the locus 860 (corresponding to distance A), the stimulation at intensity 855 is uncomfortable.

If the feedback loop were enabled when making measurements, e.g. with the target response intensity set to the value 865, the stimulus intensity would fluctuate over the posture wave. The measured (stimulus intensity, response intensity) value pairs would vary within the locus 870. Overstimulation and discomfort would thereby be avoided. For this reason, the present disclosure includes both open-loop and closed-loop implementations of estimating the patient's physiological characteristics through a posture wave in a given posture.

Open-Loop Implementations

In accordance with one implementation of the present technology, the feedback controller 310 is not used, so the module 110 operates in open-loop mode. The CI 740 may estimate the physiological characteristics of a patient in a fixed posture by instructing the device 710 to deliver pairs of stimulus pulses, one after the other separated by a short interval, and with stimulus amplitudes I varying rapidly by a small amount $\Delta I$ compared to a baseline stimulus amplitude $I_1$, for example increasing from $I_1$ to $I_1+\Delta I$ within each pair. "Varying rapidly" in the present context means that the interval between the pulses in each pair is short compared to the time it takes the electrode-cord distance to change under the posture wave. With heartbeat occurring at a ~1 s period, and breathing being slower, an interval of 20 ms between pulses (equivalent to a 50 Hz stimulus frequency) achieves this objective. The response intensity (e.g. ECAP amplitude) E is measured for each pulse in the pair, giving two measurement pairs $(I_1, E_1)$ and $(I_1+\Delta I, E_2)$ for each pair of stimulus pulses. Each pair of measurement pairs $(I_1, E_1)$ and $(I_1+\Delta I, E_2)$ may be converted to an estimate of sensitivity S and an estimate of threshold T, for example by a linear fit:

$$S = \frac{E_2 - E_1}{\Delta I} \quad (4)$$

$$T = I_1 - \frac{E_1}{S} \quad (5)$$

Figure 9A:
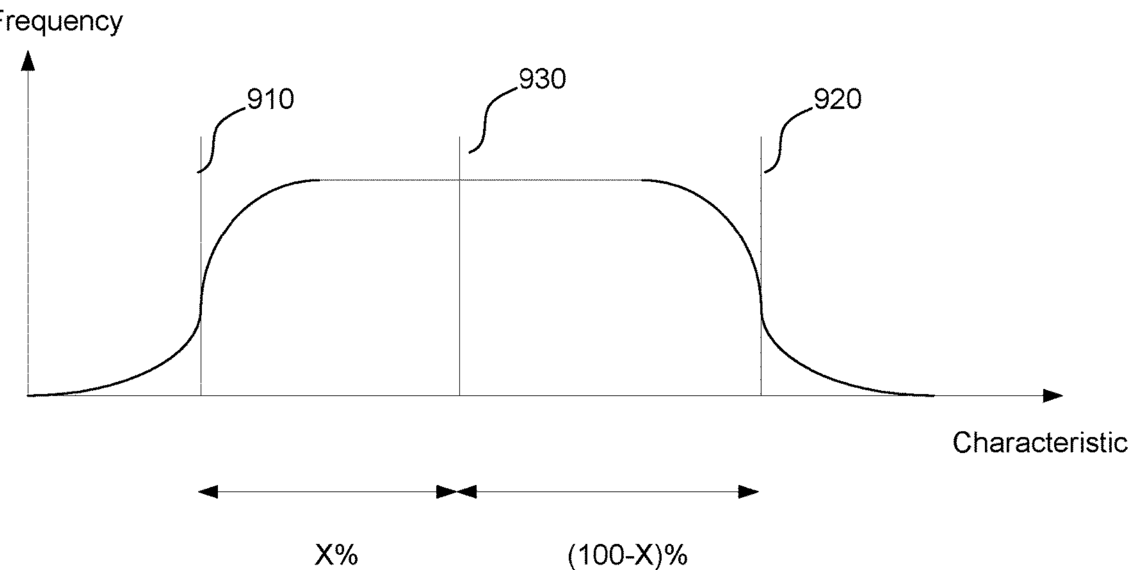
FIG. 9*a* is an example of a histogram of a time series of estimates of a physiological characteristic.

Repeating this process many times results in a time series $S(t_i)$ of sensitivity estimates S and a time series $T(t_i)$ of ECAP threshold estimates T, where the times $t_i$ are the discrete instants at which the pairs of measurements (S, T) were made. The time series $S(t_i)$ and $T(t_i)$ may be recorded in individual one-dimensional histograms that indicate the range of their respective variations over the posture wave. FIG. 9*a* is an example of such a histogram, with the bulk of the values falling within the range between lower value 910 and upper value 920. A value 930 at X % along the histogram (where X may be determined from patient data) may be chosen as the baseline value of the characteristic for the current posture.

Figure 9B:
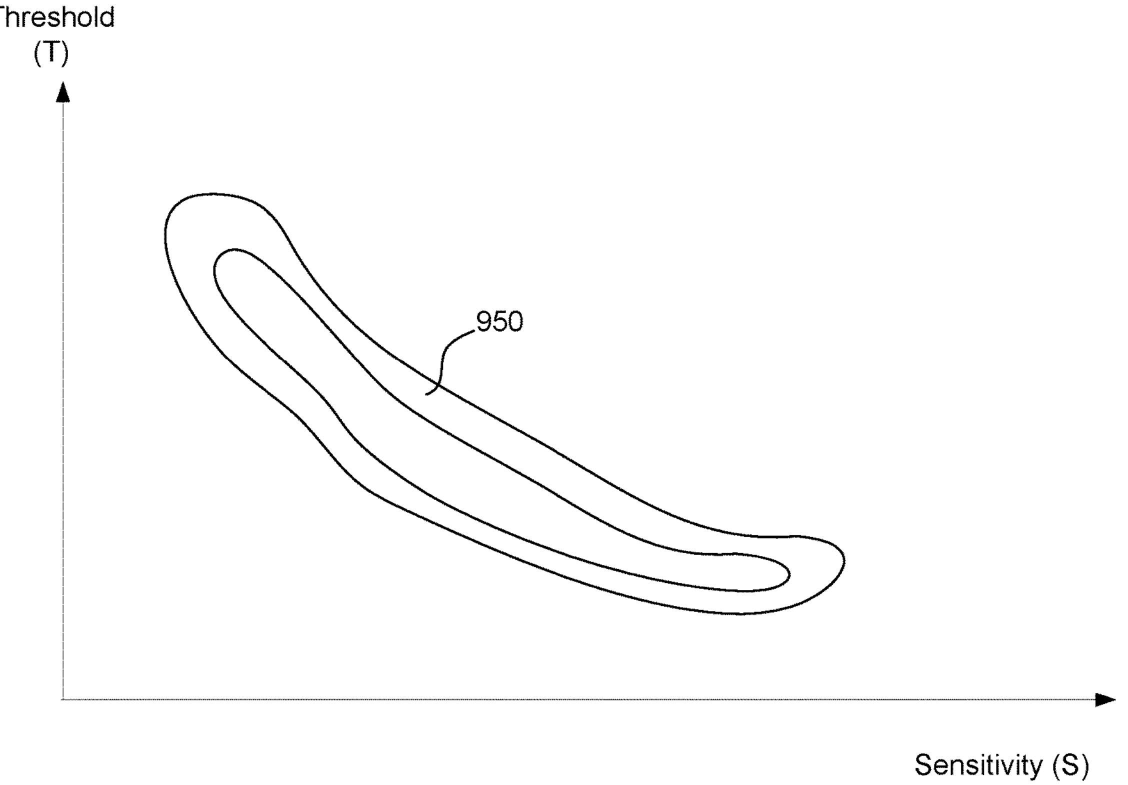
FIG. 9*b* is an example of a joint histogram of two time series of estimates of respective physiological characteristics.

The (S, T) pairs may alternatively be recorded in a joint (two-dimensional) histogram that indicates the spread of their joint variations over the posture wave. FIG. 9*b* is an example of such a histogram. The histogram of FIG. 9*a* is the projection of the two-dimensional histogram 950 onto one of the axes. Statistical moments may be extracted from the two-dimensional histogram 950 to obtain baseline values of S and T for the current posture that are robust to the posture wave, along with respective ranges of variation and covariation of those characteristics.

As an alternative to analysing histograms, the time series $S(t_i)$ and $T(t_i)$ may be analysed separately or jointly to obtain baseline values of S and T for the current posture that are robust to the posture wave, along with respective ranges of variation of those characteristics.

Figures 10A, 10B:
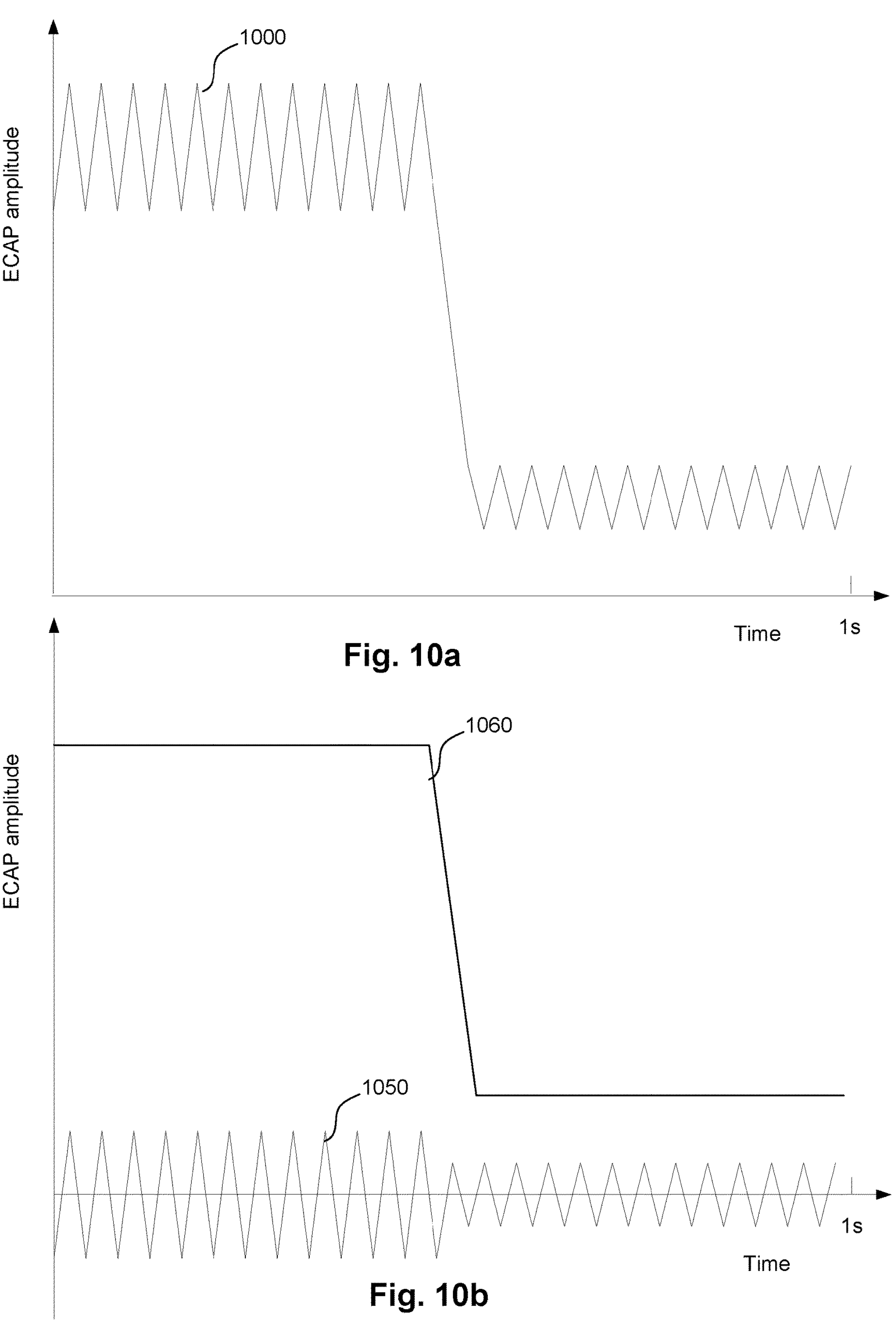
FIG. 10*a* illustrates an evoked response intensity time series resulting from a triangular stimulus intensity variation.
FIG. 10*b* illustrates the separation of the times series of FIG. 10*a* into components.

An alternative open-loop implementation also involves varying the stimulus intensity in a fixed posture and measuring the resulting response intensity. However, rather than varying stimulus intensity in discrete pairs of stimulus pulses, stimulus intensity may be varied periodically according to a waveform I(t) which oscillates with amplitude ΔI around a baseline intensity $I_0$. The period of the stimulus intensity variation should be short compared to the time it takes for the electrode-cord distance to change under the posture wave. In one example, the periodic function is a triangular waveform with frequency equal to half the stimulus frequency. As an example, a 50 Hz stimulus frequency gives a 40 ms period of stimulus intensity variation, which is short compared to the approximately one second period of heartbeat. The response intensity (e.g. ECAP amplitude) E is measured as a time series E(t). FIG. 10*a* illustrates an ECAP amplitude time series 1000 resulting from a triangular stimulus intensity variation at half of a 50 Hz stimulus frequency (40 ms period of variation). The posture wave is modelled as a 1 Hz square wave of 50% duty cycle. The ECAP amplitude time series E(t) is the sum of two components: G(S, ΔI, t) is the stimulus-induced modulation component (independent of threshold T), and F(S, T, t) is the component induced by the posture wave. The components G(S, ΔI, t) and F (S, T, t) (labelled 1050 and 1060 respectively) of the time series 1000 are illustrated in FIG. 10*b*. Note there are step changes in S and T at the midway point due to the posture wave at 1 Hz, causing step changes in G(S, ΔI, t) and F(S, T, t).

Figure 11:
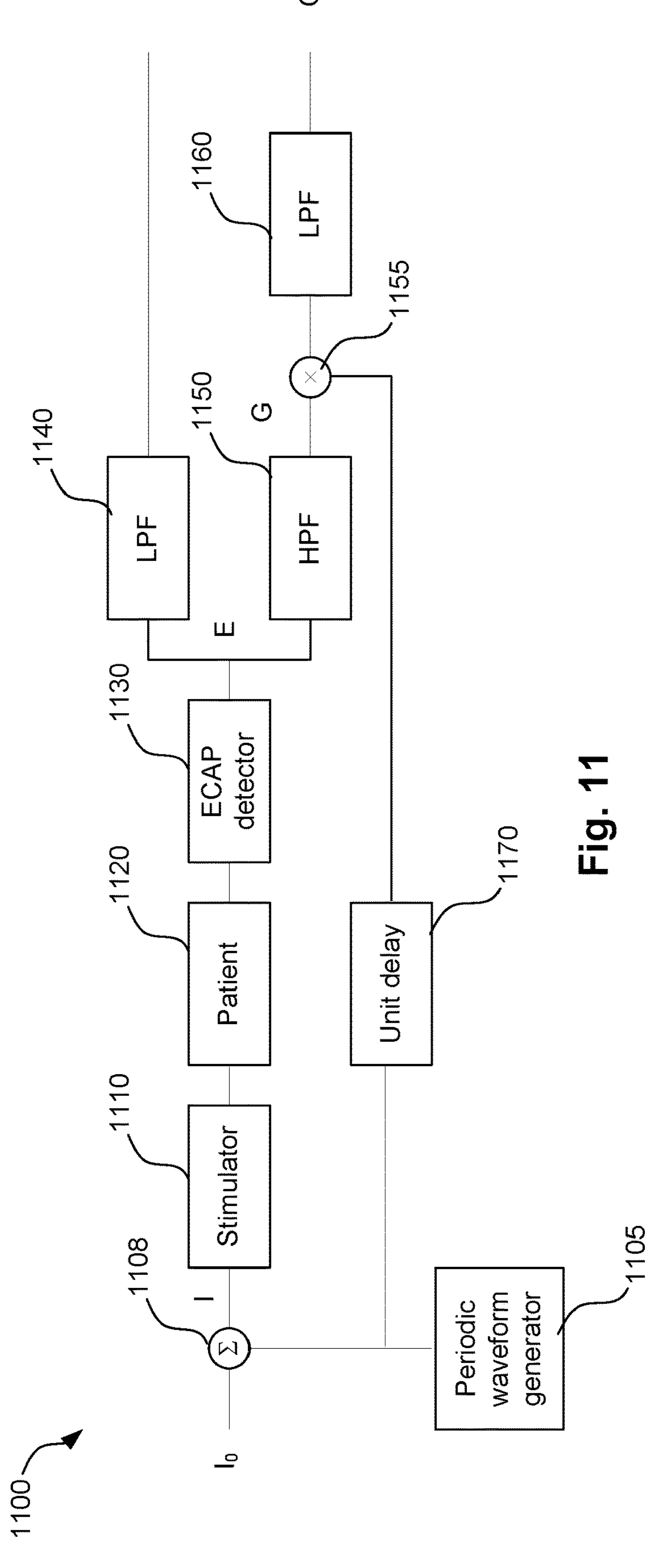
FIG. 11 is a schematic diagram of a circuit that may be used to generate a stimulus intensity waveform and separate the components in FIG. 10*b* from the evoked response intensity time series in FIG. 10*a;*

FIG. 11 is a schematic diagram of a circuit 1100 that may be used to generate the stimulus intensity waveform I(t) and separate the components G(S, ΔI, t) and F(S, T, t) from the evoked response intensity time series E(t). A periodic waveform generator 1105 generates the periodically varying stimulus intensity waveform with amplitude ΔI. The adder 1108 adds the periodic waveform to a baseline stimulus intensity $I_0$ to generate the stimulus intensity waveform I(t). The stimulator 1110 generates stimulus pulses according to the stimulus intensity waveform I(t) and delivers them to the patient 1120. The ECAP detector 1130 detects the evoked responses (ECAPs) and measures their intensities (amplitudes) to generate the response intensity time series E(t). This is passed through a low-pass filter 1140 to generate the posture wave component F(S, T, t). The cutoff frequency of the low-pass filter 1140 may be positioned midway between the stimulus intensity oscillation frequency and the anticipated frequency of the posture wave. A complementary high-pass filter 1150 generates the stimulus modulation component G(S, ΔI, t). The stimulus modulation component G(S, ΔI, t) may be demodulated to a baseband or envelope signal $G_0(S, \Delta I, t)$ by mixing it at mixer 1155 with the stimulus intensity variation waveform (delayed by a unit delay 1170) and low-pass filtering the mixed signal using low-pass filter 1160. The filters 1140, 1150, and 1160 and mixer 1155 may be implemented by a processor of the CI 740, configured by the APM as described above.

The baseband signal $G_0(S, \Delta I, t)$ may be divided by the stimulus intensity variation amplitude ΔI to give the sensitivity time series S(t). The threshold time series T(t) may be obtained from the sensitivity time series S(t) and the posture wave component F(S, T, t) using the following equation:

$$T(t) = I_0 - \frac{F(S, T, t)}{S(t)} \quad (6)$$

The time series S(t) and T(t) may be analysed separately or jointly to obtain baseline values of S and T for the current posture that are robust to the posture wave, along with respective ranges of variation of those characteristics.

Alternatively, the time series S(t) and T(t) may be placed into separate one-dimensional histograms or a joint two-dimensional histogram. The histograms may be analysed as described above in relation to FIGS. 9*a* and 9*b*, to obtain baseline values of S and T for the current posture that are robust to the posture wave, along with respective ranges of variation of those characteristics.

In an alternative implementation, the stimulus intensity variation waveform may be a different periodic waveform, such as a sinusoid or a sawtooth. The spectrum of the periodic stimulus intensity variation may be chosen to be spectrally distinct from that of the posture wave, which may be achieved in one example by choosing the frequency of the stimulus intensity variation to be substantially higher than the frequency of the posture wave, to the extent permitted by the finite stimulus frequency. The response intensity time series E(t) may be measured for several periods of the stimulus intensity variation. The stimulus modulation component G(S, ΔI, t) may be separated out of E(t) using a band-pass filter tuned to the frequency of the periodic variation. A complementary notch filter may be used to separate out the posture wave component F(S, T, t). This implementation may then proceed as in the implementation described above.

Closed-Loop Implementations

One closed-loop implementation makes use of baseline estimates of the patient's ECAP threshold T and sensitivity S and their respective ranges of variation obtained from one of the open-loop implementations described above to initialise the parameters, such as the controller gain K, for the system 300 illustrated in FIG. 5.

In this implementation, once the feedback loop is operating, and with the patient remaining in the fixed posture, a target response intensity is chosen, so the stimulus intensity fluctuates along with the posture wave in order to maintain the response intensity at the target response intensity. A representative stimulus intensity value, such as an average value, may be extracted from the fluctuation of the stimulus intensity to give a (representative stimulus intensity, target response intensity) value pair, possibly along with a range of variation of the stimulus intensity due to the posture wave. This may be repeated for a number of target response intensities, giving a number of (representative stimulus intensity, target response intensity) value pairs, each possibly accompanied by a range of variation of the stimulus intensity. An activation plot of a predetermined form, such as piecewise linear as illustrated in FIG. 4*a*, may be fitted to the value pairs, and the patient's baseline values of ECAP threshold T and sensitivity S may be extracted from the fitted activation plot for the current posture. The fitting process may also calculate confidence intervals around the fitted values of T and S reflecting the size of their variations due to the posture wave. The result would be ranges of variation of each characteristic, bounded by the highest and lowest probable values that could be extracted from the fitted activation plot.

In one implementation of extracting a representative stimulus intensity value, the component in the stimulus intensity that varies with the posture wave is tracked, for example using a phase-locked loop (PLL). The stimulus intensity is sampled at the same phase location on each posture wave cycle and the sampled values are averaged. This will reduce the variation in stimulus intensity at each target response intensity and allow a baseline activation plot to be fitted more easily to the resulting (representative stimulus intensity, target response intensity) value pairs.

In another closed-loop implementation, a perturbation is imposed on the stimulus current determined by the feedback controller 310 before delivering the stimulus to the patient.

Figure 12A:
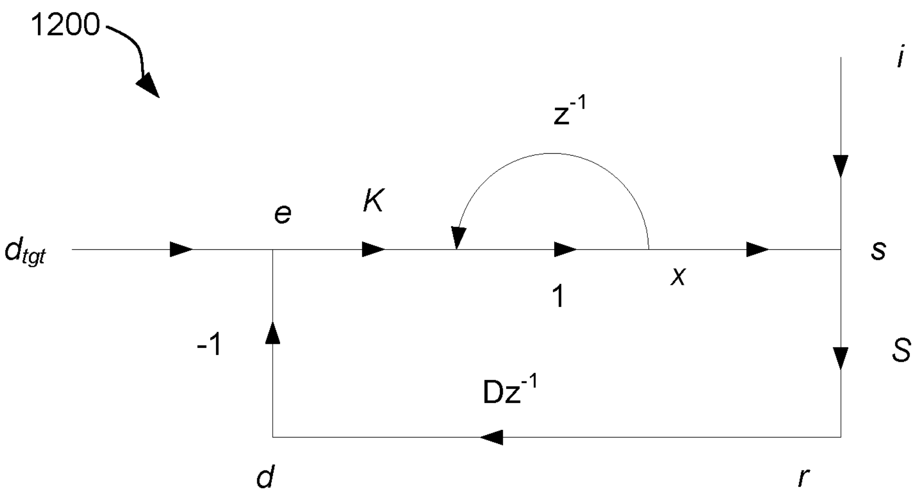
FIG. 12*a* is a discrete signal flow diagram representing the feedback loop of FIG. 5 with a perturbation summed with the stimulus current determined by the feedback controller before delivering the summed stimulus to the patient.

FIG. 12*a* is a discrete signal flow diagram 1200 representing the system 300 with a perturbation i summed with the stimulus intensity x determined by the feedback controller 310 before delivering the summed stimulus intensity s to the patient. The stimulus intensity s is transformed by the patient sensitivity S into the sensed signal r. The sampling frequency fs of the discrete signal flow 1200 is the stimulus frequency. The gain of the amplifier in the measurement circuitry 318 is D, while the ECAP detector 320 imparts a delay of one sample in measuring the ECAP amplitude d, so their concatenation is represented by the multiplier $Dz^{-1}$. The target ECAP amplitude is represented by $d_{tgt}$. The product SDK is referred to as the loop gain. In some implementations, the gain D of the amplifier is omitted as the measured ECAP is returned at its pre-amplifier magnitude.

The transfer function from the target ECAP amplitude $d_{tgt}$ to the measured ECAP amplitude d is given in the Z-transform domain by:

$$\frac{d}{d_{tgt}} = \frac{SDK}{z-(1-SDK)} \tag{7}$$

The transfer function from the stimulus intensity perturbation i to the measured ECAP amplitude d is given in the Z-transform domain by:

$$\frac{d}{i} = \frac{SD}{z}\frac{z-1}{z-(1-SDK)} \tag{8}$$

Figure 12B:
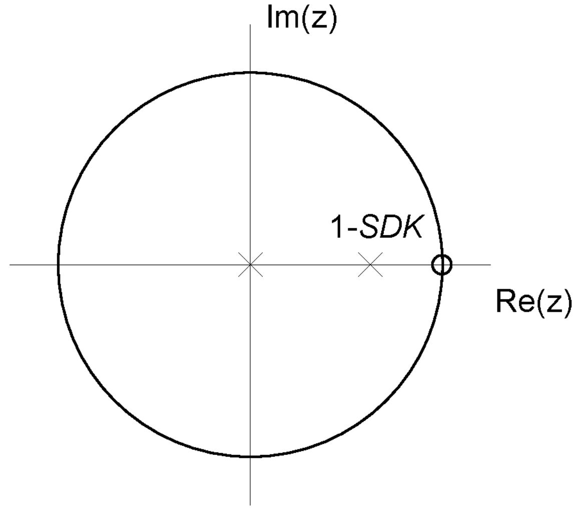
FIG. 12*b* is pole-zero plot of a transfer function of the signal flow diagram of FIG. 12*a;*

The pole-zero (Nyquist) plot of the transfer function of Equation (8) is illustrated in FIG. 12*b*, with a zero at 1 and a pole at 1-SDK. Note if K is zero, the feedback loop becomes an open loop and the pole and zero cancel each other out, giving a transfer function equal to $SDz^{-1}$. That is, the stimulus intensity perturbation i is passed unfiltered to the measured ECAP amplitude d, multiplied by the amplifier gain D and the patient sensitivity S, and delayed by one sample. If the stimulus intensity perturbation i is periodic, the magnitude g of the gain from i to d may be measured at the perturbation frequency and divided by the amplifier gain D to obtain the patient sensitivity S. This is similar to the second open-loop implementation described above.

To close the loop, the controller gain K is set to a nonzero value (i.e. the feedback loop is closed), a value for target ECAP amplitude $d_{tgt}$ is chosen, and periodic stimulus intensity perturbations i are applied at a significantly higher frequency than that of the posture wave, to the extent permitted by the finite stimulus frequency. The transfer function of Equation (8) is then a high-pass filter that attenuates low frequency cyclical anatomic perturbations relative to the higher frequency stimulus intensity perturbations. The variation in the measured response may therefore be attributed solely to the stimulus intensity perturbations. In one example, the frequency of the stimulus intensity perturbation i is set to half the stimulus frequency (z=−1), as in the open-loop implementation described above, and the magnitude g of the gain from i to d is measured. It may be shown by setting z=−1 in Equation (8) that:

$$g = \frac{2SD}{2-SDK} \tag{9}$$

Since D and K are known, the patient sensitivity S may be obtained from the gain measurement g as:

$$S = \frac{2}{D}\cdot\frac{g}{2+Kg} \tag{10}$$

In an alternative closed-loop implementation, instead of a periodic perturbation, a transient perturbation i such as a step may be added to the stimulus intensity x, and the transient response of the ECAP amplitude d may be measured. It may be shown using Equation (8) that the transient response of the ECAP amplitude d to a unit step input at i, known as the step response u[n], is $$u[n] = 1-(1-SDK)^{n+1} \tag{11}$$

Therefore, the samples of the step response u[n] are related to the loop gain SDK:

$$\frac{u[n]-u[n+1]}{u[n+1]-u[n+2]}=\frac{1}{(1-SDK)} \tag{12}$$

Since D and K are known, the baseline patient sensitivity S may be obtained from the samples of the step response u[n] as follows:

$$S=\frac{1}{DK}\left(1-\frac{u[n+1]-u[n+2]}{u[n]-u[n+1]}\right) \tag{13}$$

A similar expression for S may be obtained using Equation (7) if the step is applied to the target ECAP amplitude $d_{tgt}$ and the step response of the ECAP amplitude d is measured.

In a further closed-loop implementation, the noise n, which is an additive component of the sensed signal r as illustrated in FIG. 5, may be treated as a perturbation i of stimulus intensity. Firstly, the open-loop RMS noise $N_{OL}$ in ECAP amplitude d is measured. The controller gain may then be set to a value K, an ECAP target may be fixed, and the closed-loop RMS noise $N_{CL}$ in the ECAP amplitude d may be measured. The ratio R of the closed-loop RMS noise to the open-loop RMS noise may be computed as $R=N_{CL}/N_{OL}$. On the assumption that the noise n is white, i.e. uniformly distributed in the frequency domain, the patient sensitivity S may be estimated from the controller gain K and the ratio R of the closed-loop RMS noise to the open-loop RMS noise as:

$$S=\frac{2}{KD}\left(1-\frac{1}{R^2}\right) \tag{14}$$

In one implementation, the controller gain K is increased until the ratio R is 3 dB, i.e. $R^2=2$, at which point the controller sensitivity S is simply given by equation (14) as 1/K.

If the noise n follows a distribution that is other than uniform, the patient sensitivity may be estimated from controller gain and closed-loop to open-loop noise ratio R using a different equation than Equation (14). The equation may be derived from the noise distribution.

In alternative closed-loop implementations, the posture wave itself may be used as the perturbation of stimulus intensity, without the need for an imposed perturbation to the stimulus intensity. A periodic fluctuation in the activation plot induced by a periodic change in the electrode-cord distance, as during a posture wave, may be modelled as equivalent to a periodic perturbation Δi to the stimulus intensity at the baseline sensitivity S. The amplitude Δd of the variation of the response intensity to the equivalent periodic perturbation Δi may be measured for two different values of the controller gain K to estimate the baseline sensitivity S and, optionally, the range ΔS of variation in the sensitivity as a result of the posture wave.

In one such implementation, the controller gain K is first set to zero. The amplitude $\Delta d_0$ of the variation of the response intensity may be measured. Using Equation (8), the amplitude $\Delta d_0$ of the variation of the response intensity to the periodic intensity perturbation Δi may be shown to be given by $$\Delta d_0=SD\Delta i \tag{15}$$

However, at this stage both S and Δi are unknown.

The controller gain K may then be increased, a value for target ECAP amplitude $d_{tgt}$ is chosen, and the closed-loop response intensity variation amplitude Δd may be measured. The effect of closing the loop is to attenuate the variation in the ECAP amplitude caused by the posture wave. The controller gain K may be increased until the closed-loop response intensity variation amplitude Δd is attenuated by an amount compared to the open-loop response amplitude $\Delta d_0$. In one implementation, the amount of attenuation is determined by the preference of the patient during programming. A starting estimate for the amount of attenuation may be predetermined by measuring this parameter in a wide population of patients then using statistical methods to find the most commonly preferred value and using this value for most patients. The predetermined amount of attenuation may be adjusted if requested by the patient. In another implementation, the amount of attenuation is set to a predetermined amount such as 6 dB. The value $K_0$ of controller gain at the attenuation amount is then recorded.

The frequency $f_H$ of the posture wave may be estimated, for example using an external sensor such as a heart rate monitor in communication with the CI 740. Under the assumption that $f_H$ is much less than the sampling frequency $f_s$ (which is the case for heartbeat, for which $f_H$ is of the order of 1.2 Hz), it may be shown using Equation (8) that the amplitude Δd of variation of the response intensity to the (unknown) equivalent stimulus intensity perturbation Δi may be written as $$\Delta d=SD\frac{r}{\sqrt{r^2+(SDK_0)^2}}\Delta i \tag{16}$$

where $$r=\frac{2\pi f_H}{f_s}$$

Substituting Equation (15) into Equation (16), it may be shown that $$\frac{\Delta d}{\Delta d_0}=\frac{r}{\sqrt{r^2+(SDK_0)^2}} \tag{17}$$

which is an expression for the attenuation of the posture-wave-induced variation in ECAP amplitude achieved by closing the loop. Solving Equation (17) for the unknown baseline sensitivity S gives $$S=\frac{r}{K_0 D}\sqrt{1-\left(\frac{\Delta d}{\Delta d_0}\right)^2} \tag{18}$$

The calculated value S of baseline sensitivity may then be substituted back into the open-loop equation (15) to obtain the equivalent stimulus perturbation Δi. It may also be shown that the range ΔS of variation of sensitivity as a result of the posture wave may be computed as $$\Delta S = \frac{S^2}{d_{tgt}} \tag{19}$$

where $d_{tgt}$ is the target ECAP amplitude.

As mentioned above, the baseline estimates of the patient's ECAP threshold T and sensitivity S and their respective ranges of variation, obtained using any of the implementations described above, may be used to initialise the parameters, such as the controller gain K, for a CLNS system such as the system 300 illustrated in FIG. 5. One implementation of the setting of CLNS system parameters such as the controller gain K based on the patient sensitivity S is described in the above-mentioned Patent Cooperation Treaty Patent Publication no. WO 2016/090436. In one example, the controller gain K is set to a desired loop cutoff frequency, such as 3 Hz, divided by a value of patient sensitivity S at the maximum (most sensitive) value of its range.

Simulation Results

Figure 13A:
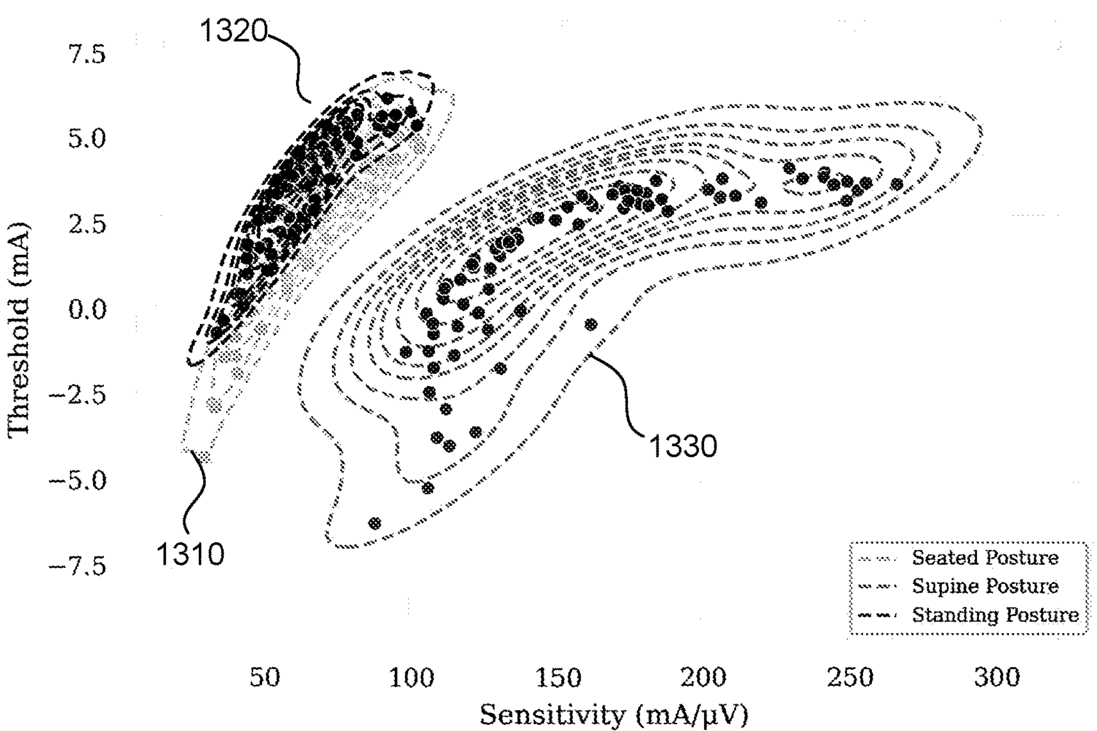
FIG. 13*a* contains joint two-dimensional histograms of estimated sensitivity S and threshold T for three different patient postures.
Figure 13B:
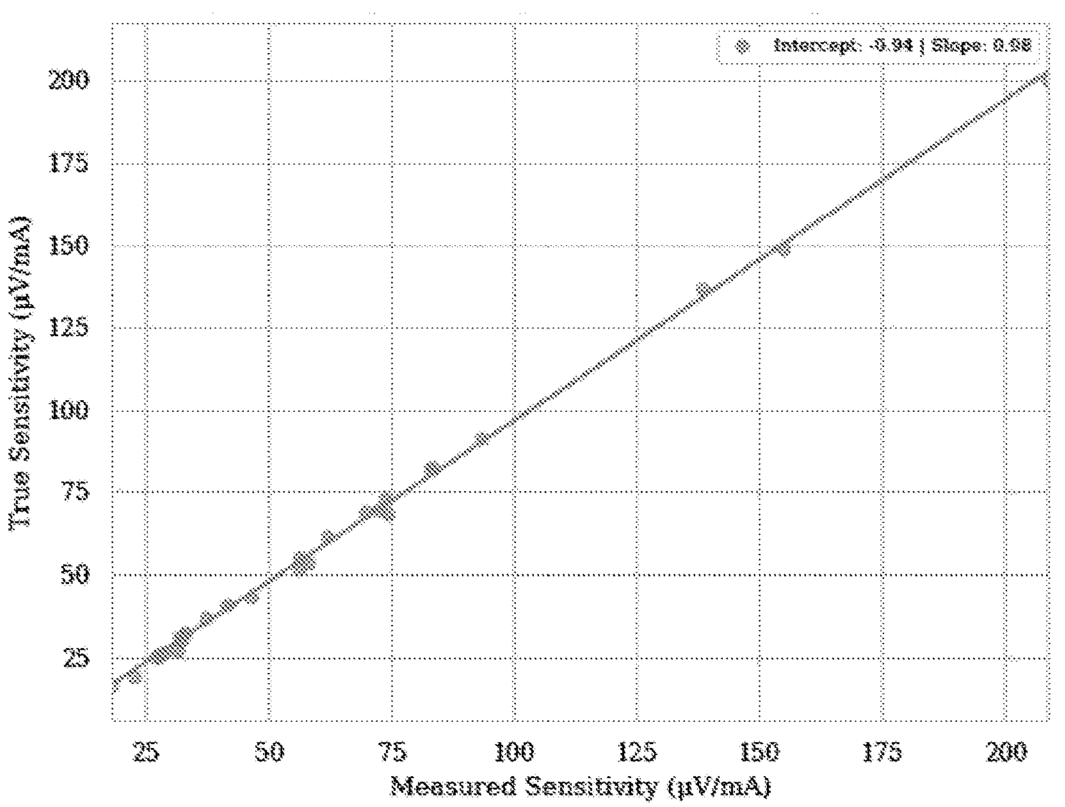
FIG. 13*b* contains a regression plot of the estimated sensitivity against the true sensitivity of the simulated patient across all three postures in FIG. 13*a;*

The pairwise variation of stimulus intensity in open-loop mode method as described above was tested on a simulated cervical patient. FIG. 13*a* contains joint two-dimensional histograms of the resulting estimated sensitivity S and threshold T for three different patient postures: seated (1310), standing (1320), and supine (1330). The variation in the characteristics caused by the posture wave is apparent for each posture, but is most noticeable for the most sensitive posture (supine). FIG. 13*b* contains a regression plot of the estimated sensitivity against the true sensitivity of the simulated patient across all three postures in FIG. 13*a*, showing good agreement between the estimated and true values.

Figure 14A:
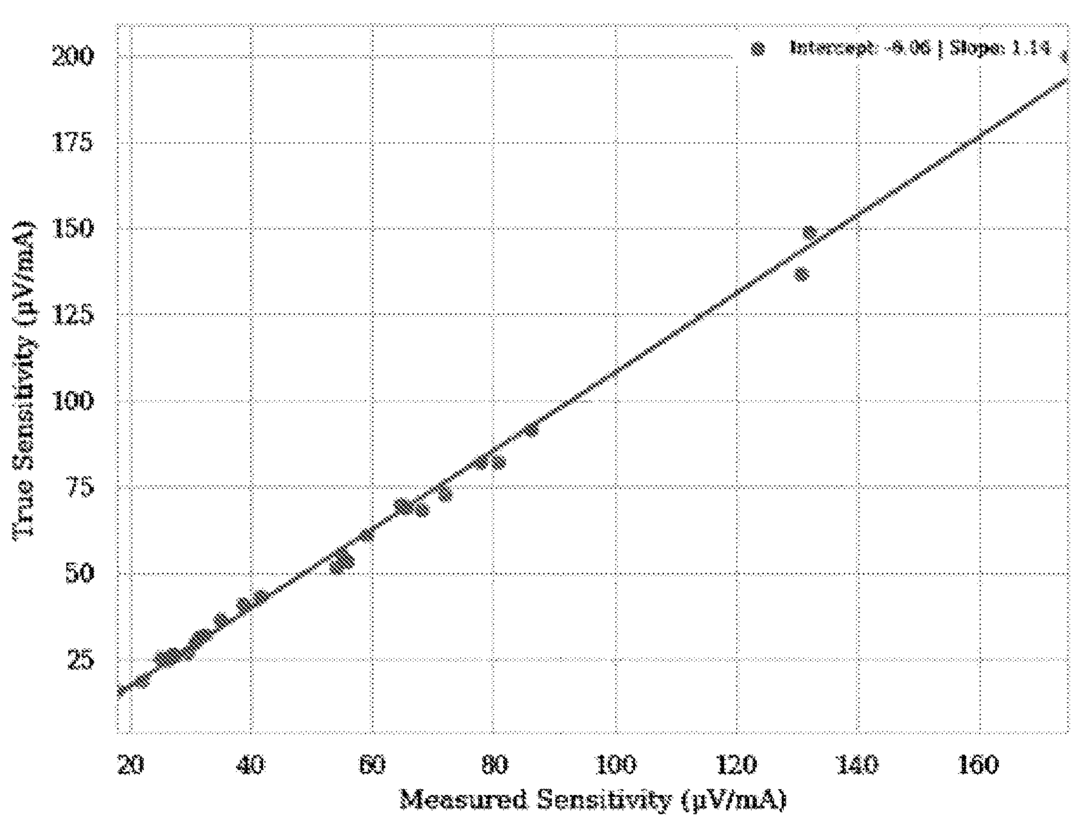
FIG. 14*a* contains a regression plot of the estimated sensitivity against the true sensitivity of the simulated patient across the same three postures as in FIG. 13*b;*
Figure 14B:
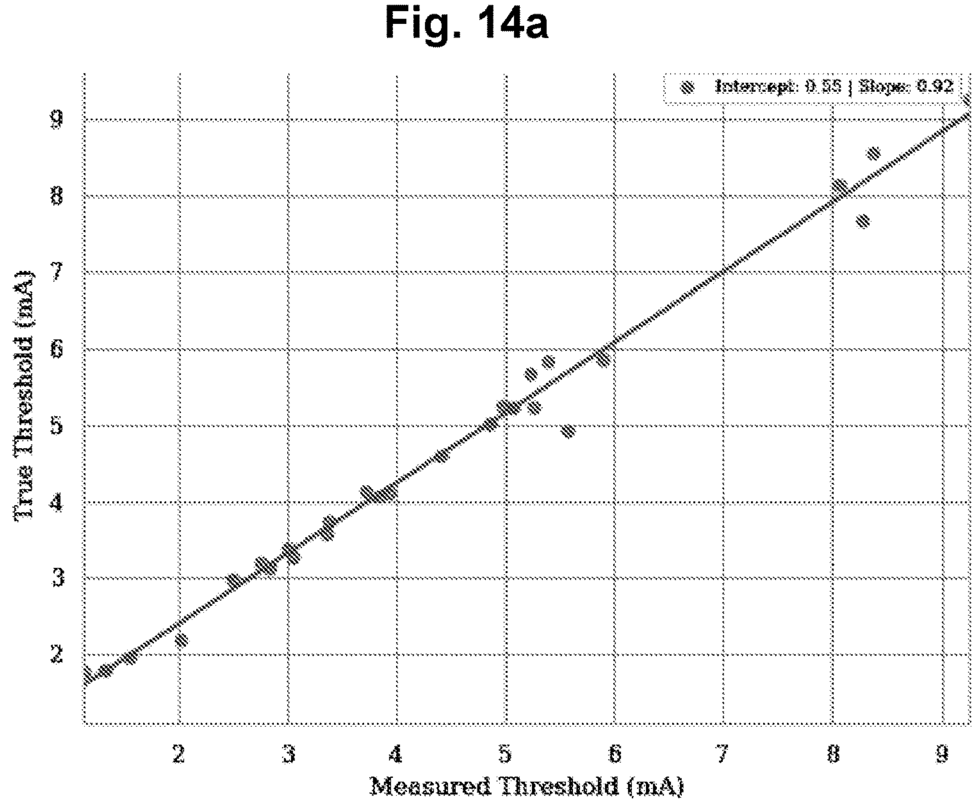
FIG. 14*b* contains a regression plot of the estimated threshold against the true threshold of the simulated patient across the same three postures as in FIG. 14*a;*

The variable-target method with PLL tracking of the posture wave in closed-loop mode as described above was also tested on a simulated cervical patient. FIG. 14*a* contains a regression plot of the estimated sensitivity against the true sensitivity of the simulated patient across the same three postures as in FIG. 13*b*, again showing good agreement between the estimated and true values. FIG. 14*b* contains a regression plot of the estimated threshold against the true threshold of the simulated patient across the same three postures as in FIG. 14*a*, again showing good agreement between the estimated and true values.

Figure 15A:
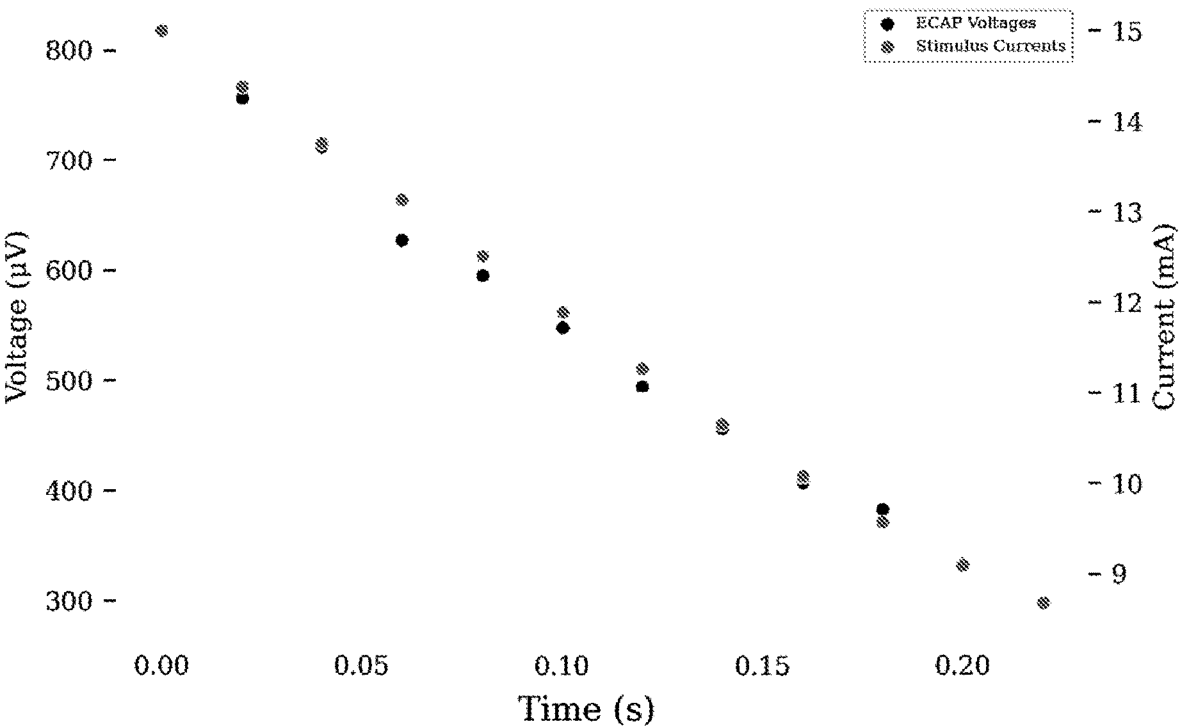
FIG. 15*a* contains a plot of the step response of both stimulus current and ECAP amplitude to a step in the target ECAP amplitude to zero.
Figure 15B:
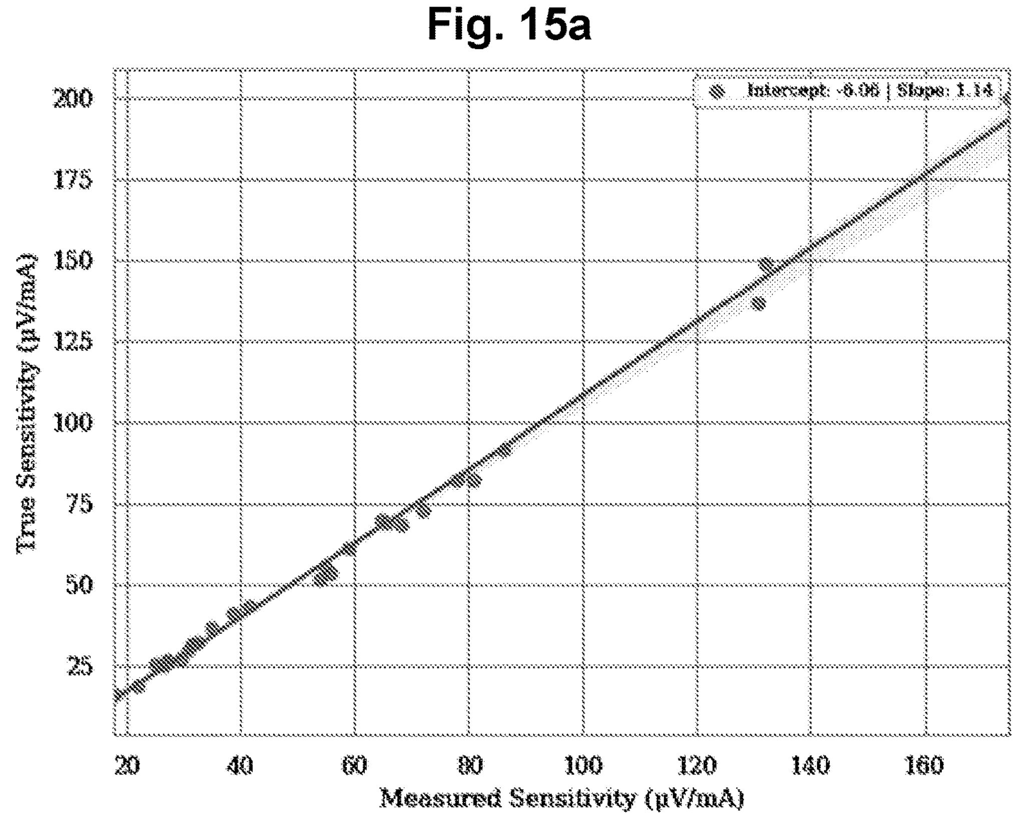
FIG. 15*b* contains a regression plot of the estimated sensitivity against the true sensitivity of the simulated patient across the same three postures as in FIG. 13*b;*

The step-response method in closed-loop mode as described above was also tested on a simulated cervical patient. FIG. 15*a* contains a plot of the step response of both stimulus current and ECAP amplitude to a down-step in the target ECAP amplitude to zero at time t=0. FIG. 15*b* contains a regression plot of the estimated sensitivity against the true sensitivity of the simulated patient across the same three postures as in FIG. 13*b*, again showing good agreement between the estimated and true values.

Figure 16:
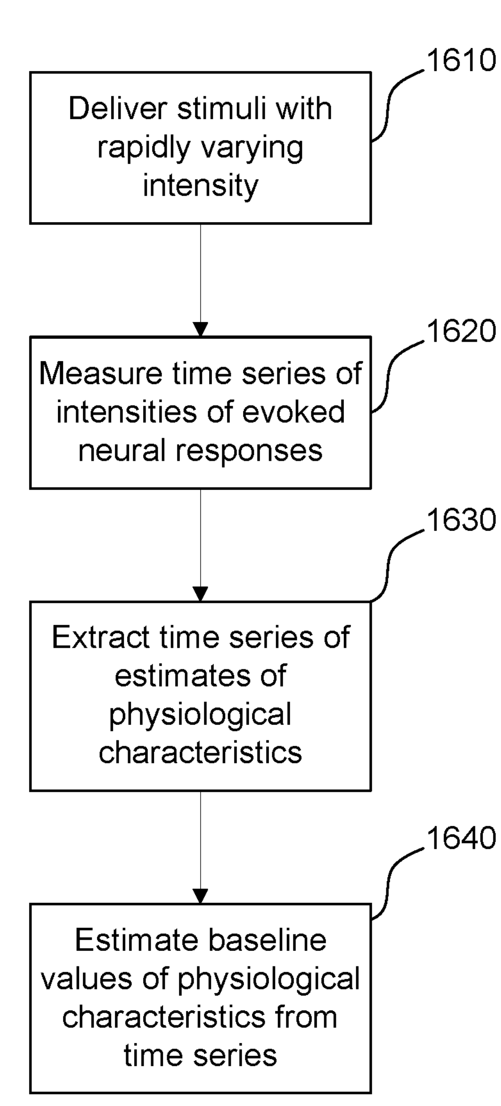
FIG. 16 contains a flow chart illustrating a method of estimating a baseline value of one or more physiological characteristics of a patient according to one implementation of the present technology.

FIG. 16 contains a flow chart illustrating a method 1600 of estimating a baseline value of one or more physiological characteristics of a patient according to one implementation of the present technology. The method 1600 starts at step 1610, which delivers a series of neural stimuli with rapidly varying intensity. Step 1620 measures a time series of intensities of neural responses evoked by the delivered stimuli. Step 1630 then extracts time series of one or more physiological characteristics from the time series of measured neural response intensities. Step 1640 then estimates the baseline values of the physiological characteristics from their respective time series.

Figure 17:
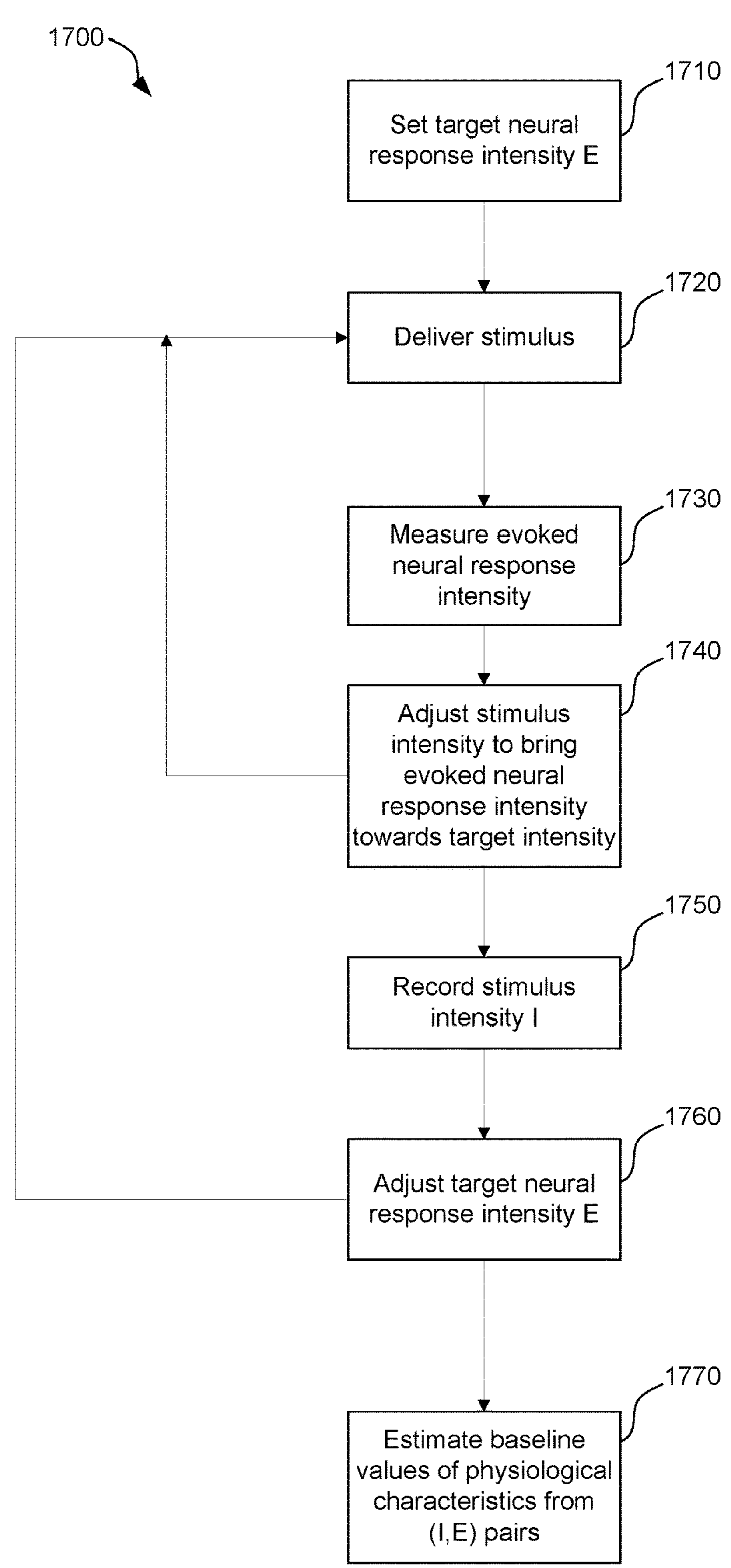
FIG. 17 contains a flow chart illustrating a method 1700 of estimating a baseline value of one or more physiological characteristics of a patient according to one implementation of the present technology.

FIG. 17 contains a flow chart illustrating a method 1700 of estimating a baseline value of one or more physiological characteristics of a patient according to one implementation of the present technology. The method 1700 starts at step 1710, which sets a target neural response intensity, labelled E. Step 1720 delivers a neural stimulus. Step 1730 measures an intensity of a neural response evoked by the delivered stimulus. Step 1740 adjusts the intensity of the delivered stimulus to bring the evoked neural response intensity toward the target neural response intensity, and cycles back to step 1720 to continue the feedback loop. When the stimulus intensity has stabilised, its value/is recorded at step 1750. Step 1760 then adjusts the target neural response intensity E, and the method 1700 returns to step 1720 to re-execute the feedback loop. After multiple iterations of step 1760, yielding multiple (I, E) pairs, the method 1700 finally moves to step 1770 which estimates the baseline values of the physiological characteristics from the (I, E) pairs.

Figure 18:
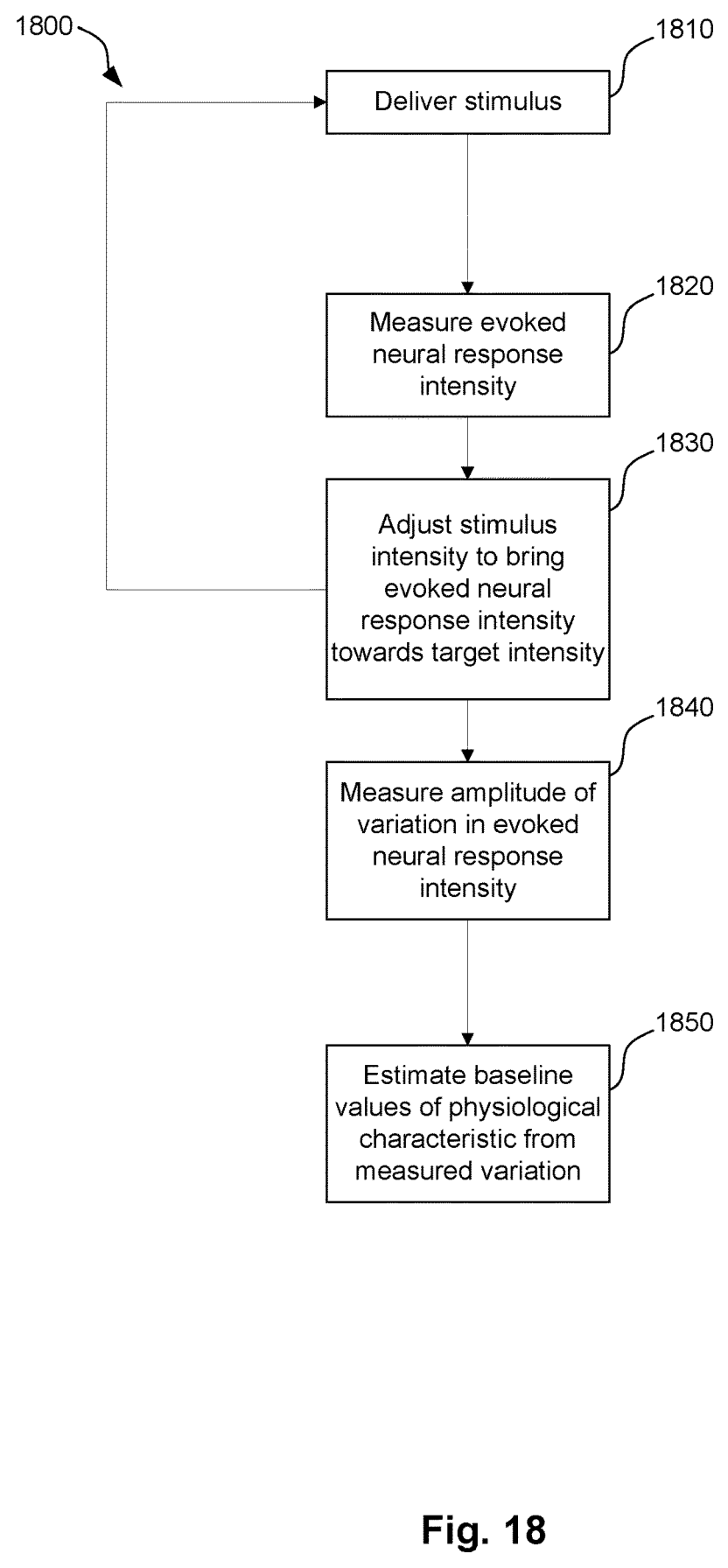

FIG. 18 contains a flow chart illustrating a method 1800 of estimating a baseline value of one or more physiological characteristics of a patient according to one implementation of the present technology. The method 1800 starts at step 1810, which delivers a neural stimulus. Step 1820 measures an intensity of a neural response evoked by the delivered stimulus. Step 1830 adjusts the intensity of the delivered stimulus to bring the evoked neural response intensity toward the target neural response intensity, and cycles back to step 1810 to continue the feedback loop. Step 1840, which may take place in parallel with steps 1810 to 1830, measures an amplitude of variation of the evoked neural response intensity. The method 1800 then moves to step 1850 which estimates the baseline values of the physiological characteristics from the measured amplitude of variation in the evoked neural response intensity.

The methods 1600, 1700, and 1800 may be implemented by a processor of the CI 740, configured by the APM as described above. Alternatively, the methods 1600, 1700, and 1800 may be implemented by the controller 116 of the device 710, configured by the APF as described above It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not limiting or restrictive.

LABEL LIST

| | |
|---|---|
| stimulator | 100 |
| patient | 108 |
| electronics module | 110 |
| battery | 112 |
| telemetry module | 114 |
| controller | 116 |
| memory | 118 |
| clinical data store | 120 |
| patient settings | 121 |
| control programs | 122 |
| pulse generator | 124 |
| electrode selection module | 126 |
| measurement circuitry | 128 |
| ground | 130 |
| electrode array | 150 |

-continued

| LABEL LIST | |
|---|---|
| biphasic stimulus pulse | 160 |
| neural response | 170 |
| nerve | 180 |
| communications channel | 190 |
| external device | 192 |
| system | 300 |
| clinical settings controller | 302 |
| target ECAP controller | 304 |
| box | 308 |
| box | 309 |
| controller | 310 |
| box | 311 |
| stimulator | 312 |
| element | 313 |
| signal amplifier | 318 |
| ECAP detector | 320 |
| comparator | 324 |
| gain element | 336 |
| integrator | 338 |
| activation plot | 402 |
| ECAP threshold | 404 |
| discomfort threshold | 408 |
| perception threshold | 410 |
| therapeutic range | 412 |
| activation plot | 502 |
| activation plot | 504 |
| activation plot | 506 |
| ECAP threshold | 508 |
| ECAP threshold | 510 |
| ECAP threshold | 512 |
| ECAP target | 520 |
| ECAP | 600 |
| neuromodulation system | 700 |
| neuromodulation device | 710 |
| remote controller | 720 |
| clinical settings transceiver | 730 |
| clinical interface | 740 |
| charger | 750 |
| graph | 800 |
| region | 810 |
| graph | 850 |
| intensity | 855 |
| locus | 860 |
| value | 865 |
| locus | 870 |
| value | 910 |
| value | 920 |
| value | 930 |
| two - dimensional histogram | 950 |
| ECAP amplitude time series | 1000 |
| component | 1050 |
| component | 1060 |
| circuit | 1100 |
| periodic waveform generator | 1105 |
| stimulator | 1110 |
| patient | 1120 |
| ECAP detector | 1130 |
| low - pass filter | 1140 |
| high - pass filter | 1150 |
| Mixer | 1155 |
| Low -pass filter | 1160 |
| unit delay | 1170 |
| discrete signal flow diagram | 1200 |
| histogram | 1310 |
| histogram | 1320 |
| histogram | 1330 |
| method | 1600 |
| step | 1610 |
| step | 1620 |
| step | 1630 |
| step | 1640 |
| method | 1700 |
| step | 1710 |
| step | 1720 |
| step | 1730 |
| step | 1740 |
| step | 1750 |
| step | 1760 |
| step | 1770 |
| method | 1800 |
| step | 1810 |
| step | 1820 |
| step | 1830 |
| step | 1840 |
| step | 1850 |

The invention claimed is:

1. A neuromodulation system comprising:

an implantable electrode array comprising a plurality of electrodes;

a stimulus source configured to provide neural stimuli to be delivered via one or more stimulus electrodes to neural tissue proximal to the implantable electrode array in order to evoke neural responses from the neural tissue, the one or more stimulus electrodes being selected from the plurality of electrodes;

measurement circuitry configured to capture signal windows sensed from the neural tissue via one or more sense electrodes subsequent to respective neural stimuli, the one or more sense electrodes being selected from the plurality of electrodes;

a control unit configured to control the stimulus source to provide the neural stimuli according to respective values of a stimulus intensity parameter; and a processor configured to:

instruct the control unit to control the stimulus source to provide the neural stimuli according to perturbed values of the stimulus intensity parameter, the perturbed values comprising a perturbation from a baseline stimulus intensity;

process the captured signal windows from the measurement circuitry in order to measure a time series of intensities of the evoked neural responses;

extract, using the measured neural response intensity time series, time series of estimates of at least one physiological characteristic of the neural tissue, wherein each physiological characteristic varies around a baseline value as a result of a posture wave; and estimate the baseline value of each physiological characteristic from the time series of estimates of each physiological characteristic.

2. The neuromodulation system of claim 1, wherein the stimulus intensity parameter perturbation comprises an oscillatory waveform with a period that is short compared to a period of the posture wave.

3. The neuromodulation system of claim 2, wherein the processor is configured to extract the time series of estimates of each physiological characteristic by separating a component of variation of the measured neural response intensity time series that is stimulus-induced from a component of variation of the measured neural response intensity time series that is induced by the posture wave.

4. The neuromodulation system of claim 1, wherein the stimulus intensity parameter perturbation comprises pairs of different intensity separated by an interval that is short compared to a period of the posture wave.

5. The neuromodulation system of claim 1, wherein the processor is configured to estimate the baseline value of one of the one or more physiological characteristics by forming a histogram of the time series of estimates of the physiological characteristic.

6. The neuromodulation system of claim 1, wherein there are a plurality of physiological characteristics, and the processor is configured to estimate the baseline value of each physiological characteristic by forming a joint histogram from the time series of estimates of each physiological characteristic.

7. The neuromodulation system of claim 1, wherein the processor is further configured to estimate a range of variation of one of the one or more physiological characteristics from the time series of estimates of the physiological characteristic.

8. The neuromodulation system of claim 1, wherein the processor is further configured to set a feedback parameter according to the baseline estimate of one of the one or more physiological characteristics.

9. The neuromodulation system of claim 8, wherein the control unit is further configured to:

process each captured signal window from the measurement circuitry in order to measure an intensity of each evoked neural response; and adjust, using the feedback parameter, the stimulus intensity parameter so as to bring the measured neural response intensity towards a target neural response intensity.

10. The neuromodulation system of claim 9, wherein the processor is further configured to:

extract a representative value of stimulus intensity parameter corresponding to the target neural response intensity;

adjust the target neural response intensity; and repeat the extracting and adjusting, yielding a plurality of (representative stimulus intensity, target response intensity) value pairs.

11. The neuromodulation system of claim 10, wherein the processor is further configured to:

estimate the baseline value of each physiological characteristic from the plurality of (representative stimulus intensity, target response intensity) value pairs.

12. The neuromodulation system of claim 11, wherein the processor is configured to estimate the baseline value of each physiological characteristic by fitting an activation plot to the plurality of (representative stimulus intensity, target response intensity) value pairs.

13. The neuromodulation system of claim 12, wherein the one or more physiological characteristics are a slope and a threshold of the fitted activation plot.

14. The neuromodulation system of claim 12, wherein the processor is further configured to calculate a confidence interval around the baseline value of each physiological characteristic.

15. The neuromodulation system of claim 1, further comprising an external computing device configured to communicate with the control unit that is co-located with, and in communication with, the measurement circuitry and the stimulus source within an implantable electronics module.

16. The neuromodulation system of claim 15, wherein the processor is part of the external computing device and is configured by program instructions stored in an instruction memory of the external computing device.

17. The neuromodulation system of claim 1, wherein the processor is part of the control unit.

18. A method of estimating a baseline value of one or more physiological characteristics of a patient, the method comprising:

delivering neural stimuli to neural tissue according to respective values of a stimulus intensity parameter in order to evoke neural responses from the neural tissue;

perturbing the stimulus intensity parameter by a small amount from a baseline stimulus intensity;

sensing on the neural tissue subsequent to respective neural stimuli and capturing signal windows from the neural tissue;

processing the captured signal windows in order to measure a time series of intensities of the evoked neural responses;

extracting, using the measured neural response intensity time series, a time series of estimates of at least one physiological characteristic of the neural tissue, wherein each physiological characteristic varies around a baseline value as a result of a posture wave; and estimating the baseline value of each physiological characteristic from the time series of estimates of each physiological characteristic.

19. A non-transitory computer readable medium for estimating a baseline value of one or more physiological characteristics of a patient, the medium comprising instructions which, when executed by one or more processors, causes performance of the following:

delivering neural stimuli to neural tissue according to respective values of a stimulus intensity parameter in order to evoke neural response from the neural tissue;

perturbing the stimulus intensity parameter by a small amount from a baseline stimulus intensity;

sensing on the neural tissue subsequent to respective neural stimuli and capturing signal windows from the neural tissue;

processing the captured signal windows in order to measure a time series of intensities of the evoked neural responses;

extracting, using the measured neural response intensity time series, time series of estimates of at least one physiological characteristic of the neural tissue, wherein each physiological characteristic varies around a baseline value as a result of a posture wave; and estimating the baseline value of each physiological characteristic from the time series of estimates of each physiological characteristic.

* * * * *